(12) United States Patent
Bumbalough

(10) Patent No.: US 8,043,372 B2
(45) Date of Patent: Oct. 25, 2011

(54) INTRAOCULAR LENS AND CAPSULAR RING

(75) Inventor: Timothy R. Bumbalough, Fullerton, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 210 days.

(21) Appl. No.: 12/265,920

(22) Filed: Nov. 6, 2008

(65) Prior Publication Data

US 2010/0094415 A1    Apr. 15, 2010

Related U.S. Application Data

(60) Provisional application No. 61/105,416, filed on Oct. 14, 2008.

(51) Int. Cl.
*A61F 2/16* (2006.01)
(52) U.S. Cl. ......... 623/6.37; 623/6.4; 623/6.49; 623/6.5
(58) Field of Classification Search .............. 623/6.51, 623/6.34, 6.37–6.49
See application file for complete search history.

(56) References Cited

U.S. PATENT DOCUMENTS

| | | |
|---|---|---|
| 4,361,913 A | 12/1982 | Streck |
| 4,370,760 A | 2/1983 | Kelman |
| 4,373,218 A | 2/1983 | Schachar |
| 4,442,553 A | 4/1984 | Hessburg |
| 4,512,040 A | 4/1985 | McClure |
| 4,560,383 A | 12/1985 | Leiske |
| 4,562,600 A | 1/1986 | Ginsberg et al. |
| 4,615,701 A | 10/1986 | Woods |
| 4,641,934 A | 2/1987 | Freeman |
| 4,731,078 A | 3/1988 | Stoy et al. |
| 4,769,035 A | 9/1988 | Kelman |
| 4,813,955 A | 3/1989 | Achatz et al. |
| 4,842,601 A | 6/1989 | Smith |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,963,148 A | 10/1990 | Sulc et al. |

(Continued)

FOREIGN PATENT DOCUMENTS

CH            681687 A5    5/1993

(Continued)

OTHER PUBLICATIONS

English translation of WO 93/05733 A1.

(Continued)

*Primary Examiner* — David H Willse
*Assistant Examiner* — Tiffany Shipmon

(57) ABSTRACT

A device includes a plurality of ringlets connected together to form a ring having a longitudinal axis. Each ringlet includes a first element and a second element. The first and second elements each extend from a first end through a central portion to a second end. The first and second ends are disposed at radially outer positions with respect to the ring than the central portion. The central portion is longitudinally displaced from the first and second ends. The first and second elements are separated and spaced apart from each other at the central portions thereof and are joined together at the first ends thereof and the second ends thereof. The ringlets are connected together such that the first ends of the elements of one ringlet are connected to the second ends of the elements of an adjacent ringlet.

25 Claims, 24 Drawing Sheets

U.S. PATENT DOCUMENTS

| | | | |
|---|---|---|---|
| 4,994,082 A | 2/1991 | Richards et al. | |
| 4,994,083 A | 2/1991 | Sulc et al. | |
| 5,047,051 A | 9/1991 | Cumming | |
| 5,152,789 A | 10/1992 | Willis | |
| 5,275,623 A | 1/1994 | Sarfarazi | |
| 5,476,514 A | 12/1995 | Cumming | |
| 5,489,302 A | 2/1996 | Skottun | |
| 5,496,366 A | 3/1996 | Cumming | |
| 5,607,472 A | 3/1997 | Thompson | |
| 5,628,795 A | 5/1997 | Langerman | |
| 5,674,282 A | 10/1997 | Cumming | |
| 5,984,962 A | 11/1999 | Anello et al. | |
| 6,013,101 A | 1/2000 | Israel | |
| 6,051,024 A | 4/2000 | Cumming | |
| 6,083,261 A | 7/2000 | Callahan et al. | |
| 6,110,202 A | 8/2000 | Barraquer et al. | |
| 6,117,171 A | 9/2000 | Skottun | |
| 6,120,538 A | 9/2000 | Rizzo, III et al. | |
| 6,197,059 B1 | 3/2001 | Cumming | |
| 6,200,342 B1 | 3/2001 | Tassignon | |
| 6,217,612 B1 | 4/2001 | Woods | |
| 6,245,102 B1 * | 6/2001 | Jayaraman | 623/1.15 |
| 6,299,641 B1 | 10/2001 | Woods | |
| 6,443,985 B1 | 9/2002 | Woods | |
| 6,797,004 B1 | 9/2004 | Brady et al. | |
| 6,930,838 B2 | 8/2005 | Schachar | |
| 7,097,660 B2 | 8/2006 | Portney | |
| 7,150,759 B2 | 12/2006 | Paul et al. | |
| 7,179,292 B2 | 2/2007 | Worst et al. | |
| 7,220,279 B2 | 5/2007 | Nun | |
| 7,300,464 B2 | 11/2007 | Tran | |
| 7,503,938 B2 | 3/2009 | Phillips | |
| 7,815,678 B2 | 10/2010 | Ben Nun | |
| 2003/0004569 A1 | 1/2003 | Haefliger | |
| 2004/0082993 A1 | 4/2004 | Woods | |
| 2004/0082995 A1 | 4/2004 | Woods | |
| 2004/0111153 A1 | 6/2004 | Woods et al. | |
| 2005/0018504 A1 | 1/2005 | Marinelli et al. | |
| 2005/0021139 A1 | 1/2005 | Shadduck | |
| 2005/0131535 A1 | 6/2005 | Woods | |
| 2006/0238702 A1 | 10/2006 | Glick et al. | |
| 2007/0078515 A1 | 4/2007 | Brady | |
| 2007/0100444 A1 * | 5/2007 | Brady et al. | 623/6.37 |
| 2007/0106381 A1 | 5/2007 | Blake | |
| 2007/0129798 A1 | 6/2007 | Chawdhary | |
| 2007/0135915 A1 | 6/2007 | Klima | |
| 2007/0213817 A1 | 9/2007 | Esch et al. | |
| 2007/0260309 A1 | 11/2007 | Richardson | |
| 2008/0161913 A1 | 7/2008 | Brady et al. | |
| 2008/0161914 A1 | 7/2008 | Brady et al. | |
| 2009/0012609 A1 | 1/2009 | Geraghty et al. | |
| 2010/0063588 A1 * | 3/2010 | Park | 623/6.23 |

FOREIGN PATENT DOCUMENTS

| | | | |
|---|---|---|---|
| EP | 766540 A1 | | 4/1997 |
| EP | 766540 B1 | | 8/1999 |
| FR | 2728459 | * | 12/1995 |
| FR | 2728458 | * | 6/1996 |
| JP | 2126847 | | 5/1990 |
| JP | 2000245755 | * | 9/2000 |
| WO | WO0119288 A1 | | 3/2001 |
| WO | WO0219949 A2 | | 3/2002 |
| WO | 2005/117748 A2 | | 12/2005 |
| WO | WO2005115278 A1 | | 12/2005 |

OTHER PUBLICATIONS

U.S. Appl. No. 09/656,661, Filed Sep. 7, 2000.
Thornton S., "Accommodation in Pseudophakia," 1991, pp. 159-162.
U.S. Appl. No. 09/721,072, filed Nov. 22, 2000.

* cited by examiner

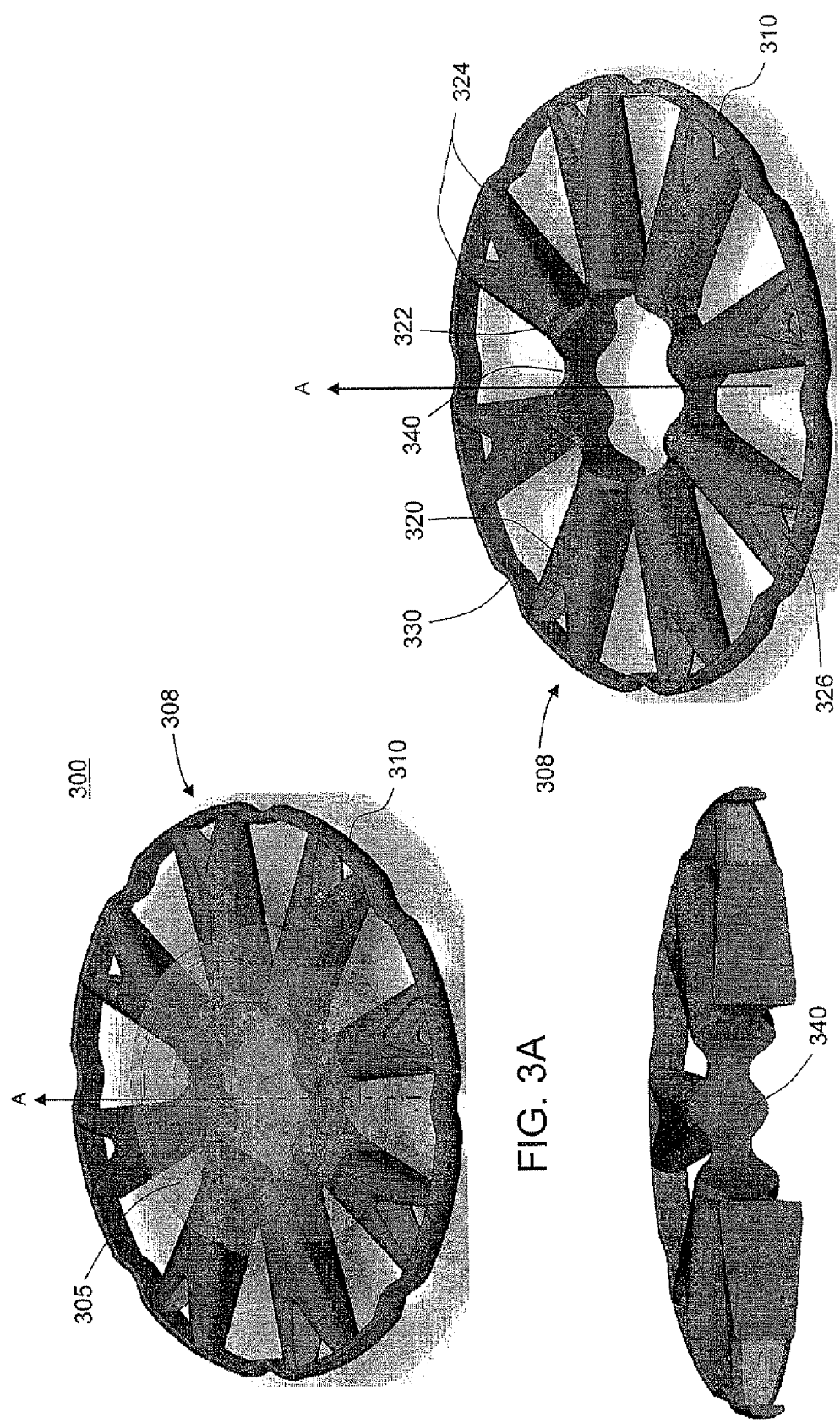

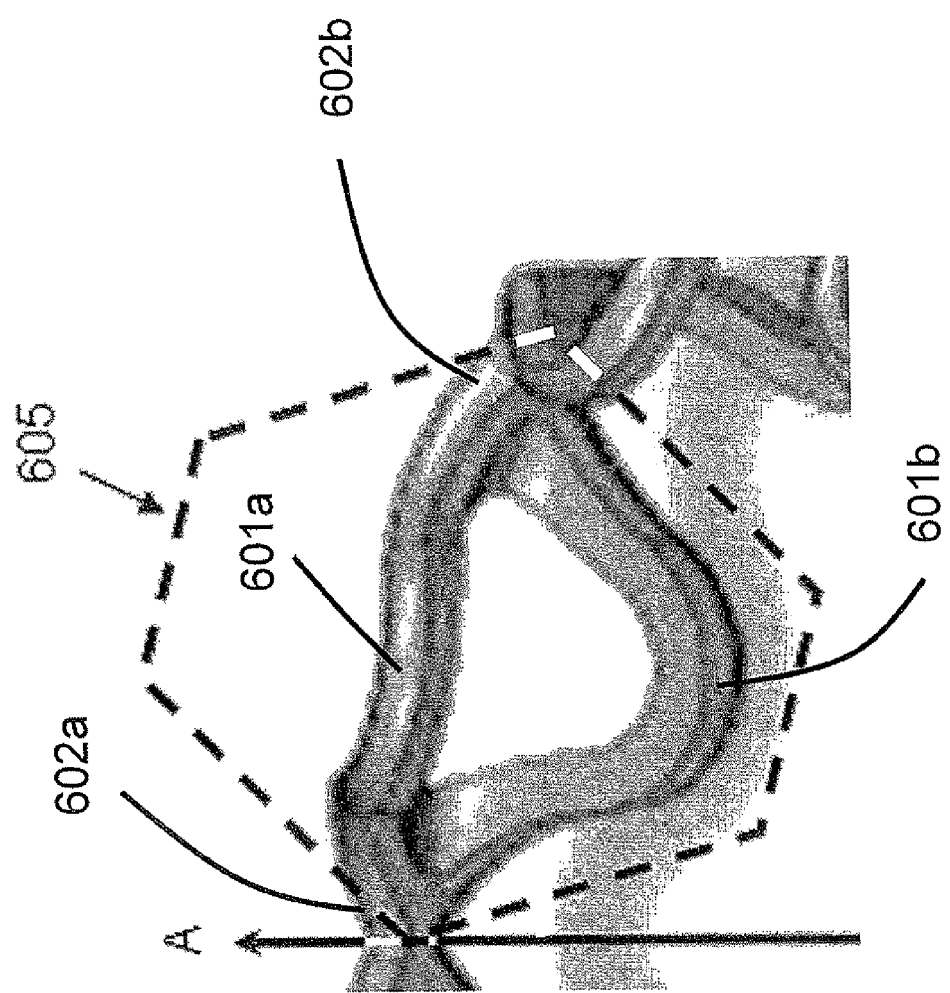

INTRAOCULAR LENS AND CAPSULAR RING

CROSS-REFERENCES TO RELATED APPLICATIONS

This patent application claims the priority benefit under 35 U.S.C. §119(e) from U.S. provisional patent application 61/105,416 filed on 14 Oct. 2008 in the name of Timothy Bumbalough et al., the entirety of which is hereby incorporated herein by reference for all purposes as if fully set forth herein.

BACKGROUND AND SUMMARY

1. Field

This invention pertains to the field of intraocular devices and procedures, and more particularly, a capsular ring for strengthening a capsular bag, for holding open a capsular bag of an eye, and/or for providing accommodation.

2. Description

A human eye can suffer diseases that impair a person's vision. For instance, a cataract may increase the opacity of the lens, causing impaired vision or blindness. To restore the patients vision, the diseased lens may be surgically removed and replaced with an artificial lens, known as an intraocular lens, or IOL. An IOL may also be used for presbyopic lens exchange.

The simplest IOLs have a single fixed focal length, or, equivalently, a single fixed power. Unlike the eye's natural lens, which can adjust its focal length and/or axial location within a particular range in a process known as accommodation, these single focal length IOLs cannot generally accommodate. As a result, distant objects may appear in focus, while objects at closer distances appear blurred.

An improvement over fixed, single focal length IOLs is an accommodating IOL, which can move axially and/or adjust its optical power within a particular range. As a result, the patient can clearly focus on objects in a range of distances away from the eye, rather than at a single distance. This ability to accommodate is of tremendous benefit for the patient and more closely approximates the patient's natural vision than a single focal length IOL.

When the eye focuses on a relatively distant object, the lens power is at the low end of the accommodation range, which may be referred to as the "distant" or "far" power. When the eye focuses on a relatively close object, the lens power and/or position is at the high end of the accommodation range, which may be referred to as the "near" power. The accommodation range or add power is defined as the actual or effective near power minus the far power. In general, an accommodation range of 2 to 4 diopters is considered sufficient for most patients.

The human eye contains a structure known as the capsular bag, which surrounds the natural lens. The capsular bag is transparent, and serves to hold the lens. In the natural eye, accommodation is initiated by the ciliary muscle and a series of zonular fibers, also known as zonules. The zonules are located in a relatively thick band mostly around the equator of the lens, and impart a largely radial force to the capsular bag that can alter the shape and/or the location of the natural lens and thereby change its actual or effective power.

In a surgery in which the natural lens is removed from the eye, a small opening is made in the front of the capsular bag through which lens material is typically broken up and vacuumed out of the eye, the rest of the capsular bag being left intact. The remaining capsular bag is extremely useful for an accommodating intraocular lens, in that the eye's natural accommodation is initiated at least in part by the ciliary muscle and the zonules through the capsular bag. The capsular bag may be used to house an accommodating IOL, which in turn can change shape and/or shift in some manner to affect the power and/or the axial location of the IOL.

In general, the IOL includes an optic which refracts and/or diffracts light that passes through it and forms an image on the retina, and a haptic, which mechanically couples the optic to the capsular bag. During accommodation, the zonules exert a force on the capsular bag, which in turn exerts a force on the optic. The force may be transmitted from the capsular bag directly to the optic, or from the capsular bag through a haptic to the optic.

A desirable optic for an accommodating IOL is one that changes shape or axially moves in response to a squeezing or expanding radial force applied largely to the equator of the optic (e.g., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force may produce a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

One challenge in replacing a natural lens with an IOL is to keep the capsular bag intact and to prevent the capsular bag from tearing or collapsing after the natural lens is removed from the eye so that the IOL can be implanted and properly positioned in the capsular bag. This problem can be exacerbated by the relatively large (e.g., 4 mm) incision that is typically required for this procedure. Since the zonules are attached both above and below the equator of the capsular bag, keeping the bag open offers potential for more effectively utilizing accommodative forces on the IOL.

Accordingly, it would be desirable to provide a device for facilitating the insertion of an intraocular lens into a capsular bag of an eye. It would also be desirable to provide such a device that can accommodate and hold an intraocular lens in the capsular bag.

In one aspect of the invention, a device includes a plurality of ringlets connected together to form a ring having a longitudinal axis. Each ringlet comprises a first element and a second element. The first and second elements each extend from a first end thereof through a central portion thereof to a second end thereof. The first and second ends of each element are disposed at radially outer positions with respect to the ring than the central portion of the element. The central portion of each element is longitudinally displaced from the first and second ends thereof. The first and second elements are separated and spaced apart from each other at the central portions thereof, and are joined together at the first ends thereof and the second ends thereof. The ringlets are connected together such that the first ends of the elements of one ringlet are connected to the second ends of the elements of an adjacent ringlet.

In another aspect of the invention, a device is provided for implantation into a capsular bag of an eye. The device comprises a ring element adapted to be inserted through an incision in the capsular bag and to hold open the capsular bag; and an optic adapted to be inserted into the capsular bag having the ring inserted therein, and to be operatively engaged with the ring so as to be held within the capsular bag. The ring element has a longitudinal axis and comprises a plurality of ringlets connected together. Each ringlet comprises a first element and a second element. The first and second elements each extend from a first end thereof through a central portion thereof to a second end thereof. The first and second ends of each element are disposed at radially outer positions with respect to the ring than the central portion of the element. The central portion of each element is longitudinally displaced from the first and second ends thereof. The first and second elements are separated and spaced apart from each other at the central portions thereof, and are joined together at the first ends thereof and the second ends thereof. The ringlets are connected together such that the first ends of the elements of one ringlet are connected to the second ends of the elements of an adjacent ringlet.

BRIEF DESCRIPTION OF THE DRAWINGS

FIGS. 3A-3C illustrate an isometric view of an intraocular lens 300 that may be implanted into the capsular bag of an eye.

FIG. 6B illustrates one ringlet of the capsular ring of FIG. 6A.

DETAILED DESCRIPTION

As described above, in a healthy human eye the natural lens is housed in a structure known as the capsular bag. The capsular bag is driven by a ciliary muscle and zonular fibers (also known as zonules) in the eye, which can compress and/or pull on the capsular bag to change its shape. The motions of the capsular bag distort the natural lens in order to change its power and/or the location of the lens, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left substantially intact in the eye, so that it may house the implanted intraocular lens.

Because the remaining capsular bag is thought to be capable of motion and shape change, initiated by the ciliary muscle and/or zonules, it is desirable that the implanted intraocular lens change its power and/or location in the eye in a manner similar to that of the natural lens. Such an accommodating lens may produce vastly improved vision over a lens with a fixed power and location that does not accommodate. In some instances, the natural lens may be replaced in a cataract-free eye, for example, to correct for presbyopia, which typically begins to develop during middle age.

Figure 1:
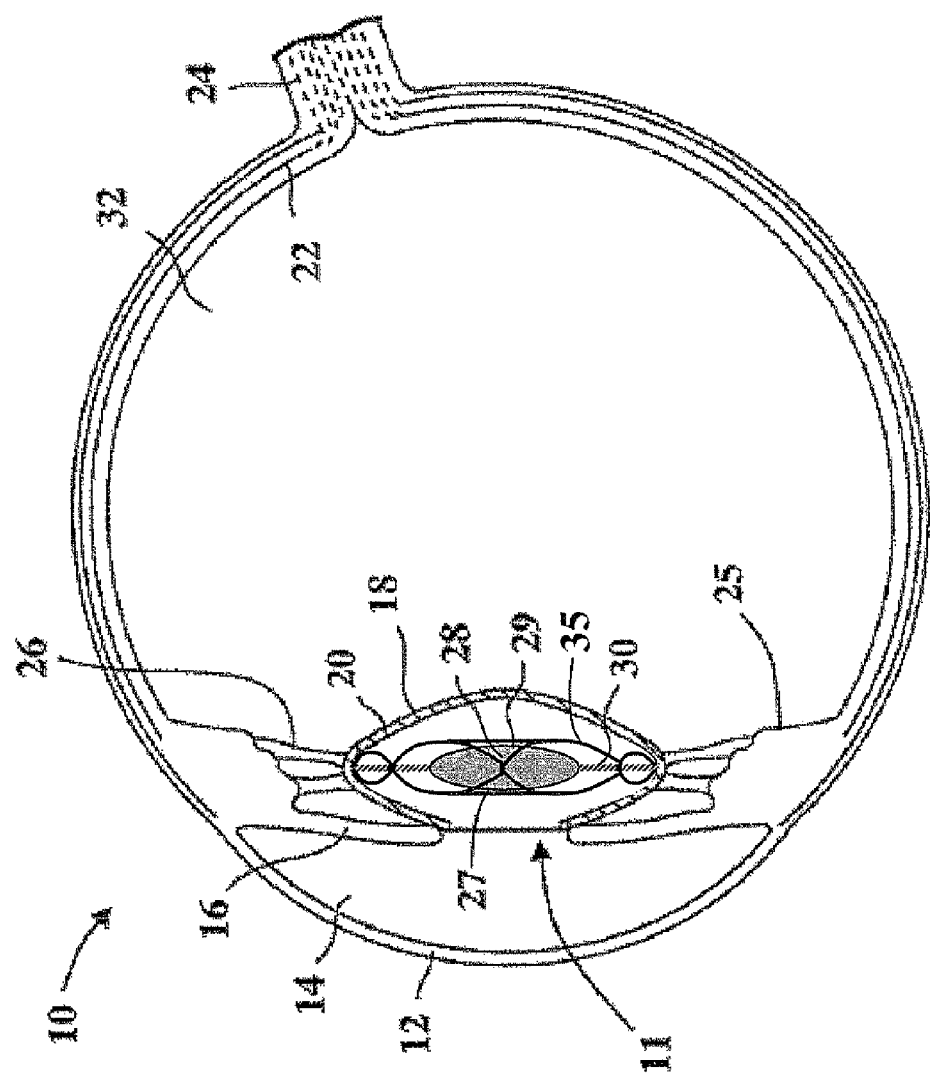
FIG. 1 illustrates a plan view of a human eye having an implanted intraocular lens, in an accommodative or "near" state.

FIG. 1 shows a human eye 10, after an accommodating intraocular lens, together with a capsular ring, has been implanted therein, in an accommodative or "near" state.

Light enters from the left of FIG. 1, and passes through the cornea 12, the anterior chamber 14, the iris 16, and enters the capsular bag 18. Prior to surgery, the natural lens occupies essentially the entire interior of the capsular bag 18. After surgery, capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of capsular bag 18, passes through the posterior chamber 32, and is focused onto the retina 22, which detects the light and converts it to a signal transmitted through the optic nerve 24 to the brain.

A well-corrected eye forms an image at retina 22. If the lens has too much or too little power, the image shifts axially along the optical axis away from the retina, toward or away from the lens. Note that the actual or effective power required to focus on a close or near object is more than the power required to focus on a distant or far object. The difference between the "near" and "far" powers is known typically as the range of accommodation. A normal range of accommodation is about 2 to 4 diopters, which is considered sufficient for most patients.

Capsular bag 18 is acted upon by the ciliary muscle 25 via the zonules 26, which changes the shape of the capsular bag 18 by stretching it radially in a relatively thick band about its equator. Experimentally, it is found that ciliary muscle 25 and/or zonules 26 typically exert a total ocular force of up to about 10 grams of force, which is distributed generally uniformly around the equator of capsular bag 18. Although the range of ocular force may vary from patient to patient, it should be noted that for each patient, the range of accommodation is limited by the total ocular force that can be exert. Therefore, it is highly desirable that the intraocular lens be configured to efficiently utilize the limited amount of ocular force to vary its power over the full range of accommodation. In other words, it is desirable to have a relatively large change in power for a relatively small driving force.

Because the ocular force is limited, it is desirable to use a fairly thin intraocular lens, compared to the full thickness of the capsular bag. In general, a thin intraocular lens may distort more easily than a very thick one, and may therefore convert the ocular force more efficiently into a change in power. In other words, for a relatively thin lens, a lower force is required to cover the full range of accommodation. In addition, utilization of larger portions of the bag disposed axially from the bag's equator may improve efficiency in converting ocular force into accommodative action.

Note that there may be an optimum thickness for the lens, which depends on the diameter of the optic. If the lens is thinner than this optimum thickness, the axial stiffness becomes too high and the lens changes power less efficiently. In other words, if the edge thickness is decreased below its optimal value, the amount of diopter power change for a given force is decreased. For instance, for an optic having a diameter of 4.5 mm, an exemplary ideal edge thickness may be about 1.9 mm, with edge thicknesses between about 1.4 mm and about 2.4 having acceptable performance as well.

Note that the lens may be designed so that its relaxed state is the "distant" or "far" condition (sometimes referred to as "disaccommodative biased"), the "near" condition ("accommodative biased"), or some condition in between the two.

Capsular bag 18 is held open by a capsular ring 35, to be described in greater detail below. In turn, capsular ring 35 accommodates the intraocular lens, for example, by utilizing a relatively large portion of the equatorial region of the capsular bag over which the zonules are attached.

The intraocular lens itself generally has two components: an optic 28, which is made of a transparent, deformable and/or elastic material, and a haptic 30, which holds optic 28 in place and mechanically transfers forces applied to capsular bag 18, to optic 28. Haptic 30 may have an engagement member with a central recess that is sized to receive the peripheral edge of optic 28.

When eye 10 focuses on a relatively close object, as shown in FIG. 1, zonules 26 relax and capsular bag 18 returns to its natural shape in which it is relatively thick at its center and has more steeply curved sides. As a result of this action, the power of the lens increases (e.g., one or both of the radii of curvature can decrease, and/or the lens can become thicker, and/or the lens may also move axially away from the retina), placing the image of the relatively close object at retina 22. Note that if the lens could not accommodate, the image of the relatively close object would be located behind retina 22, and would appear blurred.

Figure 2A:
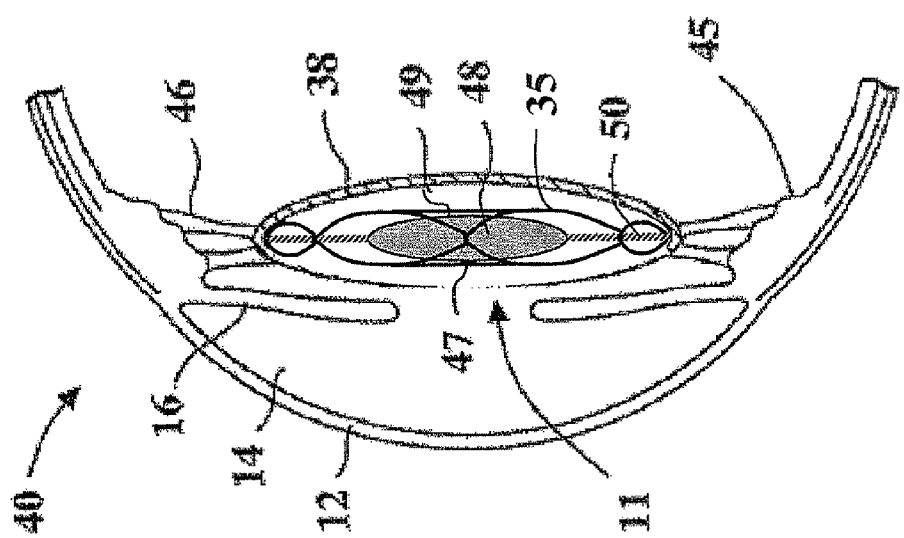
FIG. 2 illustrates a portion of a human eye in a disaccommodative or "far" state.
Figure 2B:
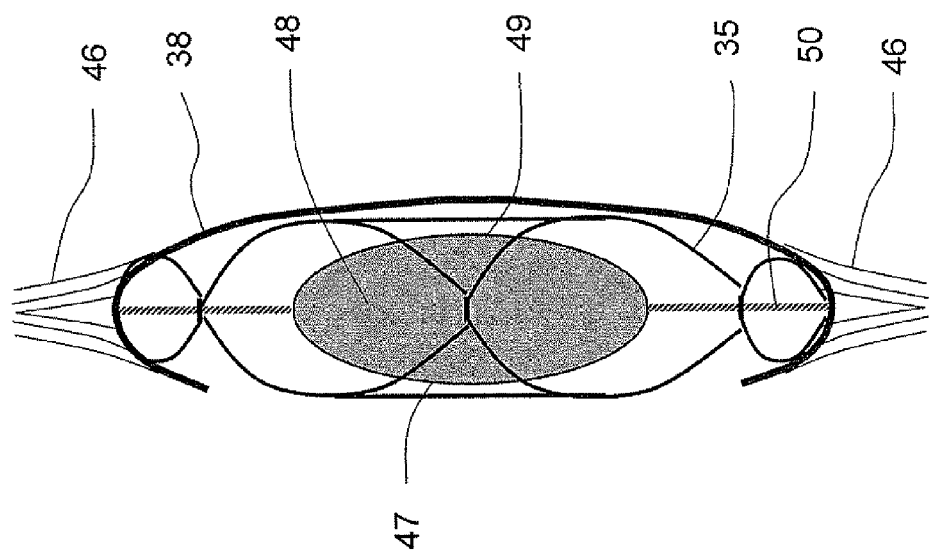

FIG. 2A illustrates a portion of an eye, after an accommodating intraocular lens together with a capsular ring has been implanted therein, in a disaccommodative or "far" state where it is focused on a relatively distant object. FIG. 2B shows a magnified view of the capsular bag 38 of FIG. 2A and structures interior thereto.

Cornea 12 and anterior chamber 14 are typically unaffected by accommodation, and are substantially identical to the corresponding elements in FIG. 1. To focus on the distant object, the ciliary muscle 45 contracts and the zonules 46 retract and change the shape of the capsular bag 38, which becomes thinner at its center and has less steeply curved sides. This reduces the lens power by flattening (i.e., lengthening radii of curvature and/or thinning) the optic (e.g., lens) 48, placing the image of the relatively distant object at the retina (not shown in FIGS. 2A-B).

For both the "near" case of FIG. 1 and the "far" case of FIGS. 2A-B, the intraocular lens itself changes shape in response to the shape changes in the capsular bag. For the "near" object, haptic 30 compresses optic 28 at its edge, increasing the thickness of optic 28 at its center and more steeply curving its anterior face 27 and/or its posterior face 29. As a result, the lens power increases. For the "far" object, haptic 50 expands, pulling on optic 48 at its edge, and thereby decreasing the thickness of optic 48 at its center and less steeply curving (e.g., lengthening one or both radius of curvature) its anterior face 47 and/or its posterior face 49. As a result, the lens power decreases.

Note that the specific degrees of change in curvature of the anterior and posterior faces of the lens depend on the nominal curvatures. Although optics (e.g., lenses) 28 and 48 are drawn as bi-convex, they may also be plano-convex, meniscus or other lens shapes. In all of these cases, the optic is compressed or expanded by essentially forces by the haptic to the edge and/or faces of the optic. In addition, there may be some axial movement of the optic. In some embodiments, the haptic is configured to transfer the generally symmetric radial forces symmetrically to the optic to deform or change the shape of the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optics may optionally have one or more diffractive elements, one or more multifocal elements, and/or one or more aspheric elements.

Embodiments of the present invention include intraocular lenses that may be configured change shape and/or traverse along an optic axis in order to provide accommodation in reaction to an accommodative ocular force, for example due forces produced by the ciliary body, zonules, capsular bag, and/or vitreous fluid of a subject eye. In certain embodiments, the accommodating intraocular lens may be disposed within a capsular ring, as discussed in greater detail below herein. Suitable intraocular lenses may include those disclosed in U.S. Patent Application Numbers 2008/0161913, 2008/0161914, which are herein incorporated in their entirety.

FIGS. 3A-3C illustrate an isometric view of an intraocular lens 300 that may be implanted into the capsular bag of an eye. The intraocular lens 300 is disposed about an optical axis OA and comprises an optic 305 and a haptic 308. Haptic 308 includes a ring potion 310 and a plurality of radial arms 320. Each radial arm 320 has a first end 322 and second ends 324 where it is connected to ring 310 and defining an opening or void 326. The openings 326 may be configured to allow the radial arms 320 to bend slightly under a radial or circumferential load, for example, due to shrinkage or fibrosis of capsular bag 18 after implantation of the intraocular lens 300. Such bending under low loading by the capsular bag 18 may be advantageously used to prevent or reduce shape changes of optic 305 under such conditions. Under heavier load conditions, for example due to an accommodative ocular force on intraocular lens 300, forces are transmitted to change the shape of optic 305 and produce an power change suitable for providing near or intermediate vision. Openings 326 maybe triangular-shaped, as in the illustrated embodiment, or have some other shape for (1) suitably deforming arms 320 under smaller load conditions such as those created by bag shrinkage or fibrosis and (2) transmitting larger accommodative loads to optic 305.

Ring portion 310 includes a plurality of indents 330, for example, disposed between and/or near each arm 320. Indents 330 may be configured to reduce the strength of, or weaken, ring portion 310 (e.g., the hoop strength). Such weakening may be advantageously used to increase the amount of external force on haptic 308 that is transmitted to optic 305 during accommodative action. In the illustrated embodiment, the indents 330 are inward toward optic 305;

however, other configurations are anticipated (e.g., an outward indent away from optic 305). Other means may be incorporated to reduce the strength of ring portion 310. For example, all or portions of ring portion 310 may have a reduce thickness, either radially, along the optical axis of intraocular lens 300, or both radially and along the optical axis of intraocular lens 300. In other embodiments, ring portion 310 may be discontinuous, containing breaks at one or more circumferential locations.

Intraocular lens 300 may also include an inner ring portion 340, for example, to connect first ends 322 of arms 320 to a common structure. In cross-section (e.g., in a plane parallel to, and passing through, optical axis OA), inner ring portion 340 may have a constant height and/or width around the entire circumference thereof. The cross-section of inner ring portion 340 may be square, rectangular, circular, oval, triangular, or the like. As shown in FIGS. 3B, 3C, the axial thickness may vary along the circumference of inner ring portion 340. In the illustrated embodiment, inner ring 340 has an axial thickness in the region of haptic arms 320 that is greater than the axial thickness between adjacent haptic arms 320.

The scallop or undulating pattern seen in FIGS. 3B, 3C of inner ring 340 may be advantageously configured to provide a path for material flow when optic 305 is formed by injection molding after fabrication of haptic 308 (either by machining or molding). In some embodiments, inner ring portion 340 may additionally or alternatively include radial apertures or through-holes for similar purposes. Additionally or alternatively, inner ring portions 340 may be configured to weaken or reduce the strength thereof.

In certain embodiments, haptic arms 320, ring portion 310, and/or inner ring portion 340 are configured to induce a predetermined, asymmetric distribution of forces onto optic 305. For example, haptic 308 may include four arms 320 circumferentially disposed 90 degrees apart from one another. In such embodiments, one pair of opposite arms 320 are configured to transmit more force to optic 305 than the other pair of opposite arms 320, whereby optic 305 becomes cylindrically shaped in response to an accommodative ocular force. Such induced cylindrical shaping of optic 305 may be used to correct an astigmatism of an eye or to provide an astigmatic aberration configured to produce an extended depth of focus in a subject eye and in response to an accommodative ocular force. Alternatively, one or both optical surfaces of optic 305 may have a cylindrical shape when in an unstressed state, whereby the four arms 320 may be configured to reduce or eliminate the amount of cylinder shape or astigmatic power of optic 305. In some cases, the four arms may be configured to further increase the amount of cylinder shape or astigmatic power of optic 305. The pair of opposite arms 320 that are configured to transmit more force to optic 305 may have a different cross-sectional height, width, and/or area that the pair of opposite arms 320 configured to transmit less force to optic 305. Additionally or alternatively, one pair of opposite arms 320 may be made of a material is less stiff or may have a lower tensile strength than the other pair of opposite arms 320. In certain embodiments, haptic 308 has more than four arms circumferentially disposed about haptic 308, whereby opposite arms 320 are configured to transmit different amounts of force to optic 305, depending on their circumferential position.

Intraocular lens 300 may be configured to provide other types of higher order aberrations. For example, haptic 308 may comprise three arms 320 that are configured to increase or decrease an amount of trefoil of optic 305 in response to an accommodative ocular force. The trefoil aberration may be configured to increase a depth of focus of optic 305 in response to the accommodative ocular force. One or more additional arms may be circumferentially disposed between pairs of the three arms 320, for example, to maintain the optic 305 in a desired orientation with the optical axis OA. In such embodiments, the additional arms may be generally less rigid and/or transmit less force to optic 320 in response to an accommodative ocular force than the three arms 320.

In yet other embodiments, the arms 320 may be configure to provide coma, for example, in an amount that is effect to produce an increased depth of focus in a subject eye. For example, pairs opposite arms 320 (e.g., circumferentially separated by 180 degrees) may be configured to transmit different amounts of force to optic 305 in response to an accommodative ocular force. This may be accomplished by constructing one arm 320 to be stiffer or more rigid than an opposite arm 320.

Combinations of the aberrations may be provided by configuring the arms 320 and/or rings segments 330, 340.

Figure 4:
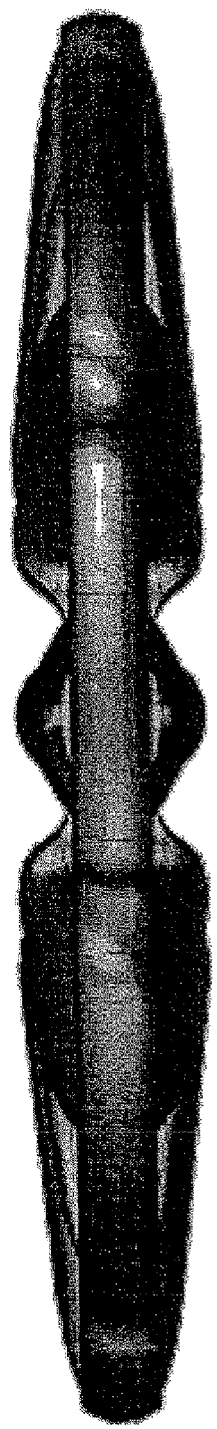
FIG. 4 illustrates a side-view of the haptic of FIG. 3.

FIG. 4 illustrates a side-view of the haptic 308.

Figure 5:
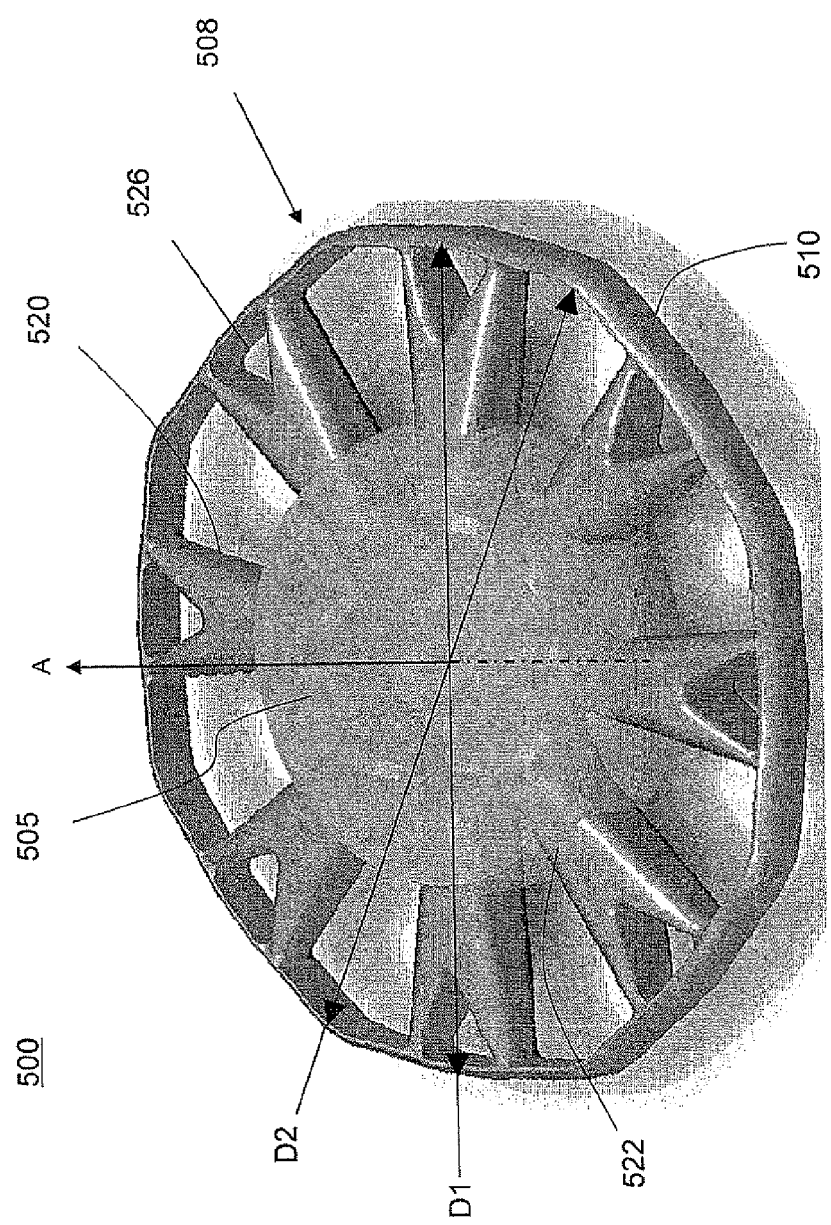
FIG. 5 illustrates an isometric view of an intraocular lens comprising an optic and a haptic coupled to optic.

FIG. 5 illustrates an isometric view of an intraocular lens 500 comprising an optic 505 and a haptic 508 coupled to optic 505. Beneficially, optic 505 comprises an intraocular lens (IOL). Even more beneficially, optic 505 comprises an accommodating IOL (A-IOL). Elements and features of intraocular lens 300 may be incorporated into intraocular lens 500, where appropriate, and visa versa.

As seen in FIG. 5, first ends 522 of radial arms 520 are adapted to be coupled to a side edge or wall of optic 505, and are each attached to an outer ring 510. Beneficially, optic 505 in FIG. 5 may have one or more annular recesses (not shown) around its side edge, and the first ends 522 of the radial arms 520 of haptic 508 extend or protrude into these annular recesses, instead of merely contacting optic 505 at a cylindrical edge parallel to the optical axis "A."

This protrusion of haptic 508 into the edge of optic 505 may allow for greater transfer of forces from the capsular bag, through haptic 508, to optic 505. There may be a greater coupling of these forces to the anterior and/or posterior surfaces of optic 505, which may result in more deforming of these surfaces for a given force. As a result, the limited capsular bag force may produce a greater deformation of optic 505, and, therefore, a larger change in power and/or a larger axial translation of the image at the retina.

Optic 505 is made from a relatively soft material, so that it can deform or change shape readily under the limited deforming force initiated by the capsular bag and transmitted through haptic 508. An exemplary material is a relatively soft silicone material, although other suitable materials may be used as well. The stiffness of optic 505 may be less than 500 kPa, or preferably may be between 0.5 kPa and 500 kPa, or more preferably may be between 25 kPa and 200 kPa, or even more preferably may be between 25 kPa and 50 kPa.

In contrast with optic 505, haptic 508 is made from a relatively stiff material, so that it can efficiently transmit the deforming forces from the capsular bag to optic 505. An exemplary material is a relatively stiff silicone material, although other suitable materials may be used as well, such as acrylic, polystyrene, or clear polyurethanes. Haptic 508 may beneficially be stiffer than optic 505. The stiffness of haptic 508 may be greater than 500 kPa, or preferably may be greater than 3000 kPa.

Because haptic 508 extends into optic 505 in a region around its radial circumference, it also may extend into the clear aperture of optic 505. For this reason, haptic 508 may beneficially be transparent or nearly transparent, so that it does not substantially block any light transmitted through optic 505.

In addition, it is desirable that the interface between optic 505 and haptic 508 does not produce any significant reflections, which would produce scattered light within the eye, and would appear as a haze to the patient. A convenient way to reduce the reflections from the interface is to match the refractive indices of haptic 508 and optic 505 to each other.

A simple numerical example shows the effect of mismatch of refractive indices on reflected power. For a planar interface at normal incidence between air (refractive index of 1) and glass (refractive index of 1.5), 4% of the incident power is reflected at the interface. For such an interface between air and glass, there is no attempt to match refractive indices, and this 4% reflection will merely provide a baseline for comparison. If, instead of 1 and 1.5, the refractive indices differ by 4%, such as 1.5 and 1.56 or 1.5 and 1.44, there is a 0.04% reflection, or a factor of 100 improvement over air/glass. Finally, if the refractive indices differ by only 0.3%, such as 1.5 and 1.505 or 1.5 and 1.495, there is a 0.00028% reflection, or a factor of over 14000 improvement over air/glass. In practice, tolerances such as the 0.3% case may be achievable, and it is seen that a negligible fraction of power may be reflected at the interface between a haptic and an optic whose refractive indices differ by 0.3%. Note that the above base value of 1.5 was chosen for simplicity, and that haptic 508 and optic 505 may have any suitable refractive index.

Beneficially, the refractive indices of haptic 508 and optic 505 are essentially the same. For the purposes of this document, "essentially the same" means that their refractive indices are equal to each other at a wavelength within the visible spectrum (i.e., between 400 nm and 700 nm). Note that haptic 508 and optic 505 may optionally have different dispersions, where the refractive index variation, as a function of wavelength, may be different for the haptic and the optic. In other words, if the refractive indices of haptic 508 and optic 505 are plotted as a function of wavelength, they may or may not have different slopes, and if the two curves cross at one or more wavelengths between 400 nm and 700 nm, then the refractive indices may be considered to be essentially the same or essentially equal.

The outer ring 510 of haptic 508 mechanically couples the intraocular lens to the capsular bag of the eye. In one embodiment, optic 505 may be molded directly onto haptic 508. Alternatively, optic 505 may be manufactured separately from haptic 508, then attached to haptic 508. Outer ring 510 is configured to have two outer diameters D1, D2, where D2 is greater than D1. In the illustrated embodiment, D1 is the outer diameter of outer ring 510 along opposite pairs of radial arms 520, while D2 is the outer diameter of outer ring 510 between adjacent pairs of radial arms 520. D1, D2 are advantageously selected to allow the intraocular lens 500 to accommodate a range of capsular bag sizes that is generally superior to a substantially equivalent outer ring that is circular or even oval in shape, or that includes indents that protrude inwardly toward the center of the intraocular lens. For example, the larger diameter D2 provides for at least portions of a capsular bag having a diameter of, or about equal to, D2 to contact the outer ring 510 when the eye is in a disaccommodative state, whereby accommodative forces may be effectively transmitted to optic 505. Alternatively, if the capsular bag has a diameter of, or about equal to, D1, then the capsular bag will contact the outer ring about its entire circumference. The capsular bag may be slightly taut over portions of ring 505 having the diameter D2, but the overall stress on the capsular bag is less than that experienced for a ring having a constant outer diameter of D2. Accordingly, the outer ring 510 of intraocular lens 500 is favorably configured to accommodate a larger variation of bag sizes than a substantially equivalent intraocular lens having an outer ring with a constant outer diameter. In certain embodiments, the outer diameter D2 is between 20 microns and 500 microns greater than the outer diameter D1, preferably between 40 microns and 250 microns greater than the outer diameter D1.

Once optic 505 is formed on, attached to, or placed within haptic 508, beneficially radial arms 520 of haptic 508 protrude into the side edge of optic 505. The axial thickness (i.e., along an axis parallel to the optical axis "A" passing through the center of the optic 505) of the portions of haptic 508 disposed within the side edge of optic 505 may be selected to control the amount and/or distribution of an ocular force acting on optic 505. For example, in some embodiments, the performance (e.g., the change Diopter power of the optic 505 between accommodative and disaccommodative configurations) increases as the edge thickness increases. In such embodiments, other design constraints (e.g., optical performance or physical constraints of the eye) may, however, place an upper limit on the maximum optic edge thickness. In some embodiments, the portion of haptic 508 inside the optic 505 has a maximum axial thickness that is at least one half a maximum axial thickness of optic 505 along the optical axis. In other embodiments, the outer ring 510 of haptic 508 has a maximum axial thickness that is at least 75% of a maximum axial thickness of the central zone.

In certain embodiments, optic 505 is a multifocal optic. In some embodiments, optic 505 may change from a monofocal optic to a multifocal optic, depending upon the amount of ocular force on haptic 508 and/or the state of accommodation of the eye into which device 500 is inserted.

As discussed above, one challenge in replacing a natural lens with a device such as device 500 is to keep the capsular bag intact and to prevent the capsular bag from collapsing after the natural lens material is removed from the eye so that device 500 can be implanted in the capsular bag and properly positioned.

Figure 6A:
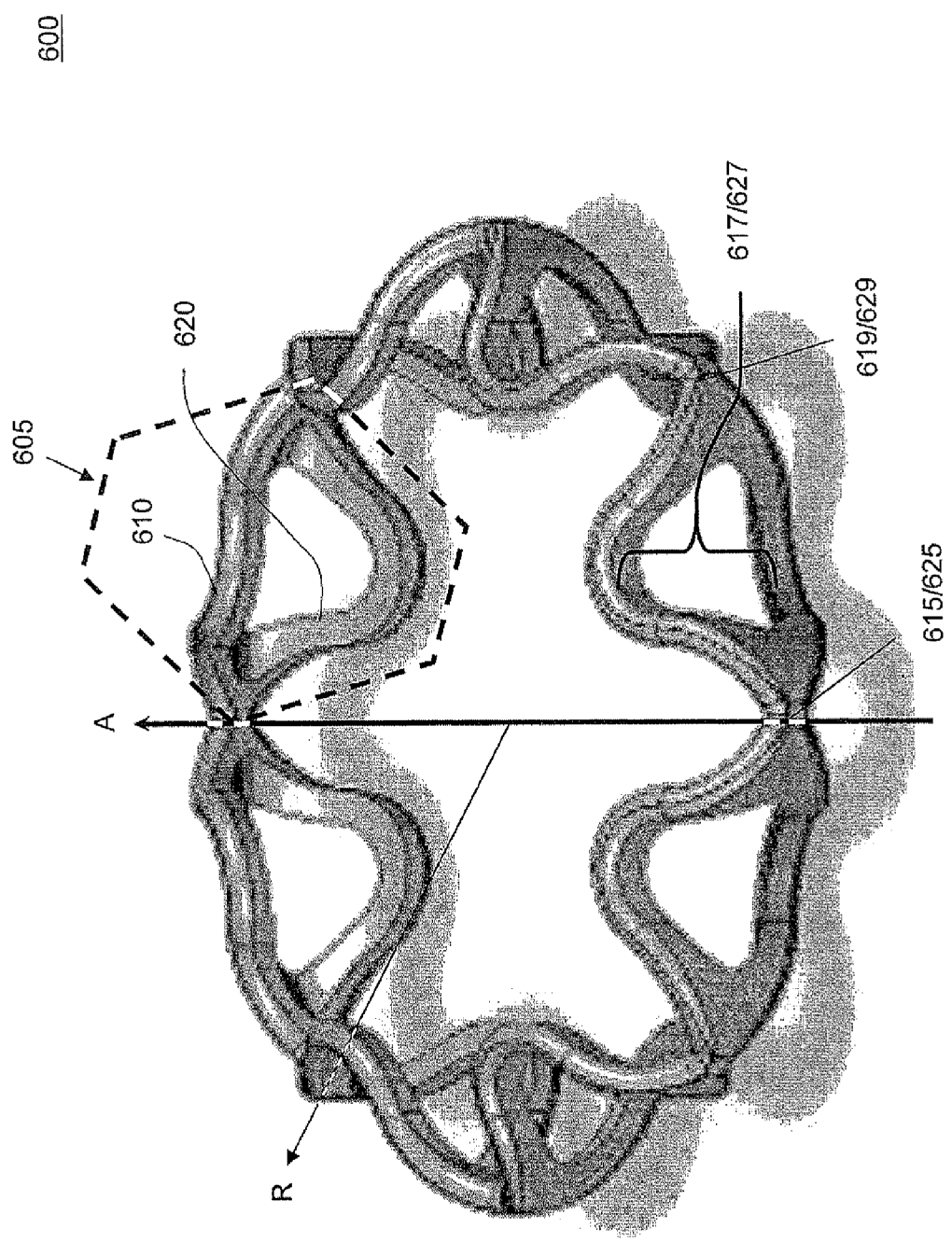
FIG. 6A illustrates an isometric view of one embodiment of a capsular ring.

Accordingly, FIG. 6A illustrates an isometric view of one embodiment of a capsular ring 600 for insertion into the capsular bag of an eye.

Capsular ring 600 includes a plurality of ringlets 605 connected together in a closed ring shape about a longitudinal axis "A." Each ringlet 605 comprises a first element 610 and a second element 620. The first and second elements 610 and 620 each extend from a respective first end 615/625 thereof, through a central portion 617/627 thereof to a second end 619/629 thereof. The first ends 615/625 and second ends 619/629 of elements 610 and 620 of each ringlet 605 are disposed at radially outer positions with respect to a radial direction "R" of the capsular ring 600 than the respective central portions 617/627 of elements 610 and 620. The central portion 617/627 of each respective element 610/620 is longitudinally displaced by an amount "X" (see FIG. 22) from the first end 615/625 and second end 619/629 thereof. The first and second elements 610 and 620 are separated and spaced apart from each other at the central portions 619/629 thereof and are joined together at the first ends 615/625 thereof and the second ends 619/629 thereof. The ringlets 605 are connected together such that the first ends 615/625 of the elements 610/620 of one ringlet 605 are connected to the second ends 619/629 of the elements 610/620 of an adjacent ringlet 605.

FIG. 6B illustrates in greater detail one ringlet 605 of capsular ring 600. As illustrated in FIG. 6B, each ringlet 605 includes first and second minor portions 601a and 601b, and first and second major portions 602a and 602b. First and second minor portions 601a and 601b are disposed at respective first and second minor radial distances from the longitudinal axis "A" and are longitudinally separated and spaced apart from each other. The first and second major portions 602*a* and 602*b* are disposed at respective first and second major radial distances from the longitudinal axis "A" that are greater than both minor radial distances. In a beneficial embodiment, the first minor radial distance is equal to second minor radial distance and the first major radial distance is equal to the second major radial distance. Capsular ring 600 is completely open and free of material above and below the major surface portions 602*a* and 602*b*. The ringlets 605 are connected together such that a major portion 601*a* of one ringlet 605 is connected to a major portion 602*b* of an adjacent ringlet 605.

Figure 7:
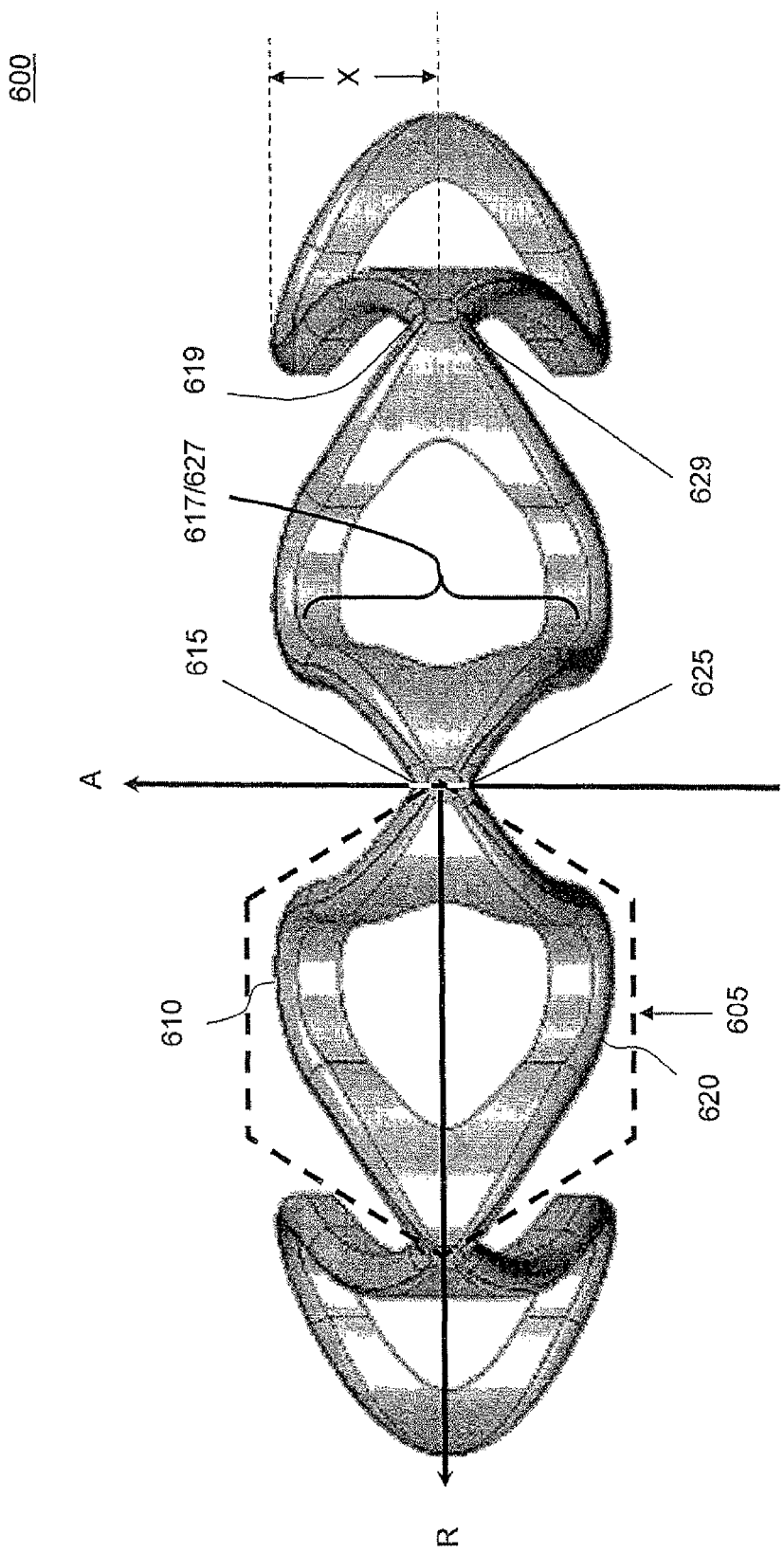
FIG. 7 illustrates a side-view of the capsular ring of FIG. 6A.
Figure 8:
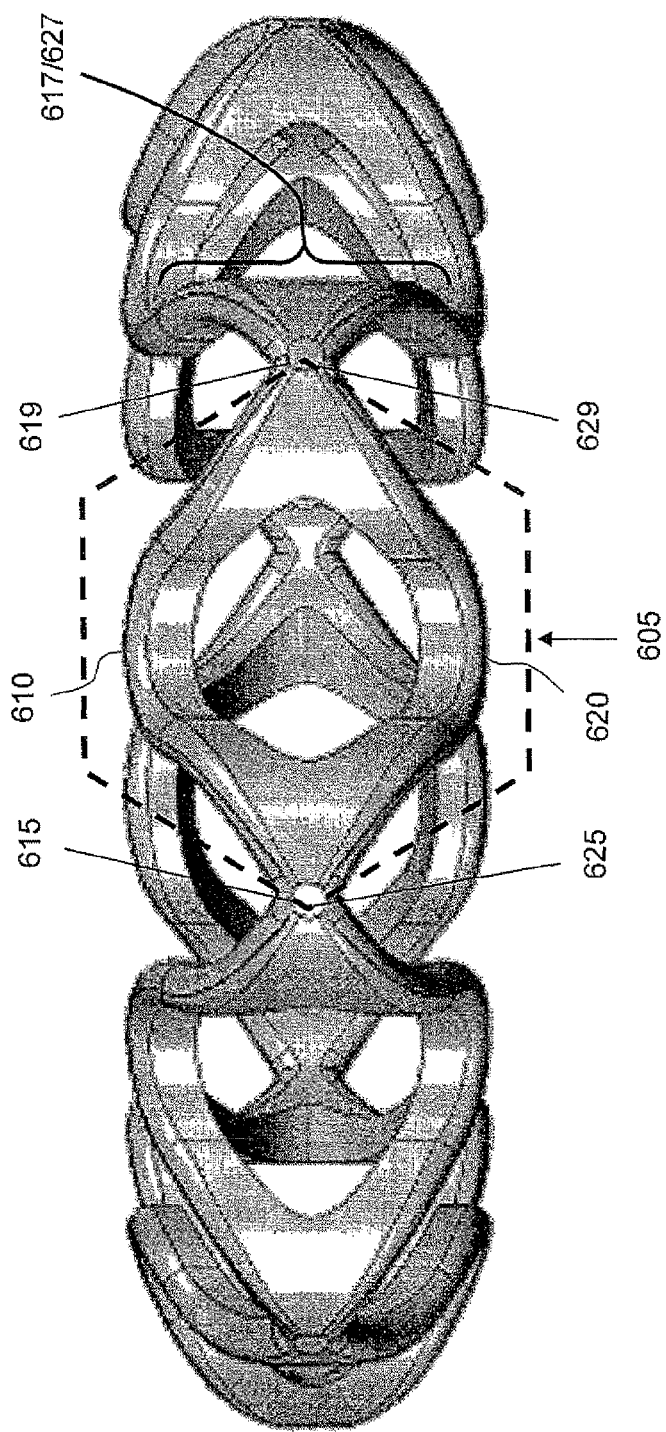
FIG. 8 illustrates another side-view of the capsular ring of FIG. 6A.
Figure 9:
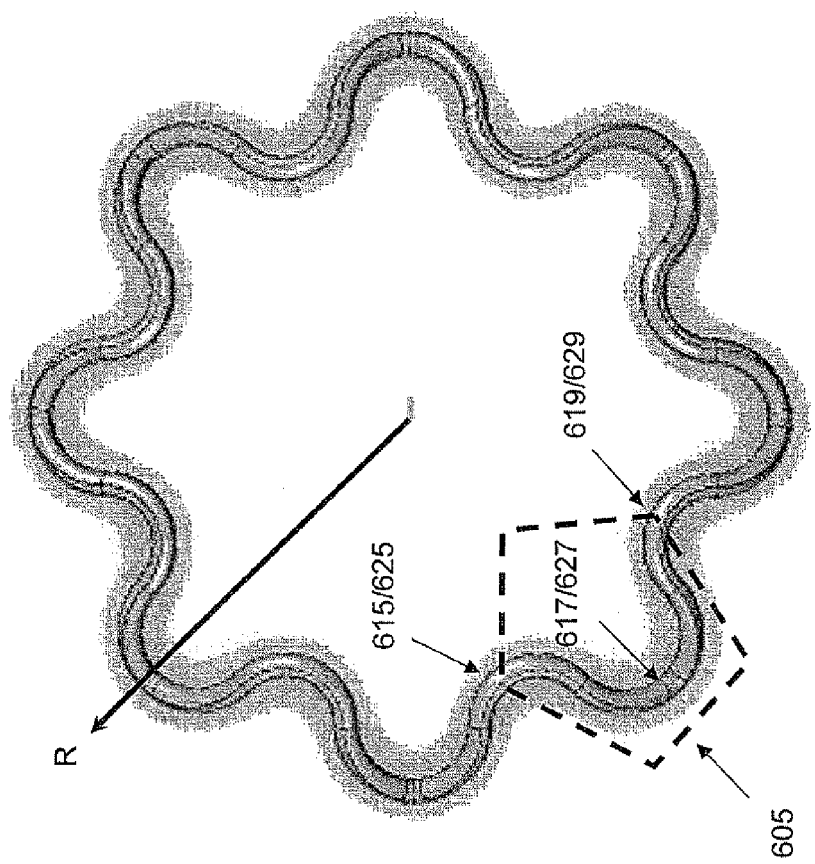
FIG. 9 illustrates a top-view of the capsular ring of FIG. 6A.

FIG. 7 illustrates a side-view of capsular ring 600. FIG. 8 illustrates another side-view of capsular ring 600. FIG. 9 illustrates a top-view of capsular ring 600.

Beneficially, capsular ring 600 is more rigid in a direction along the longitudinal axis "A" than in the radial direction "R." Also beneficially, capsular ring 600 is sized to fit within a capsular bag of a human eye and to hold the capsular bag open. Furthermore, advantageously, when capsular ring 600 is inserted into the capsular bag, it is adapted to respond to force applied to the capsular bag by zonules of the eye to change a thickness of the capsular ring 600 in a direction along the longitudinal axis "A." More particularly, as can be understood with reference to FIGS. 6-8, when a radially compressive force is applied to capsular ring 600, it causes central portions 617 and 627 of first and second elements 610 and 627 to separate further apart from each other so as to increase the dimension "X" shown in FIG. 7.

Beneficially, capsular ring 600 comprises at least one of a silicone and an acrylic material. Beneficially, capsular ring 600 is compressible so as to be adapted for insertion into the capsular bag via an incision of less than 2 mm, even more beneficially, about 1.5 mm. Advantageously, in inner diameter of capsular ring 600 reduces upon insertion into the capsular bag of an eye to conform to and indicate bag size.

Figure 10:
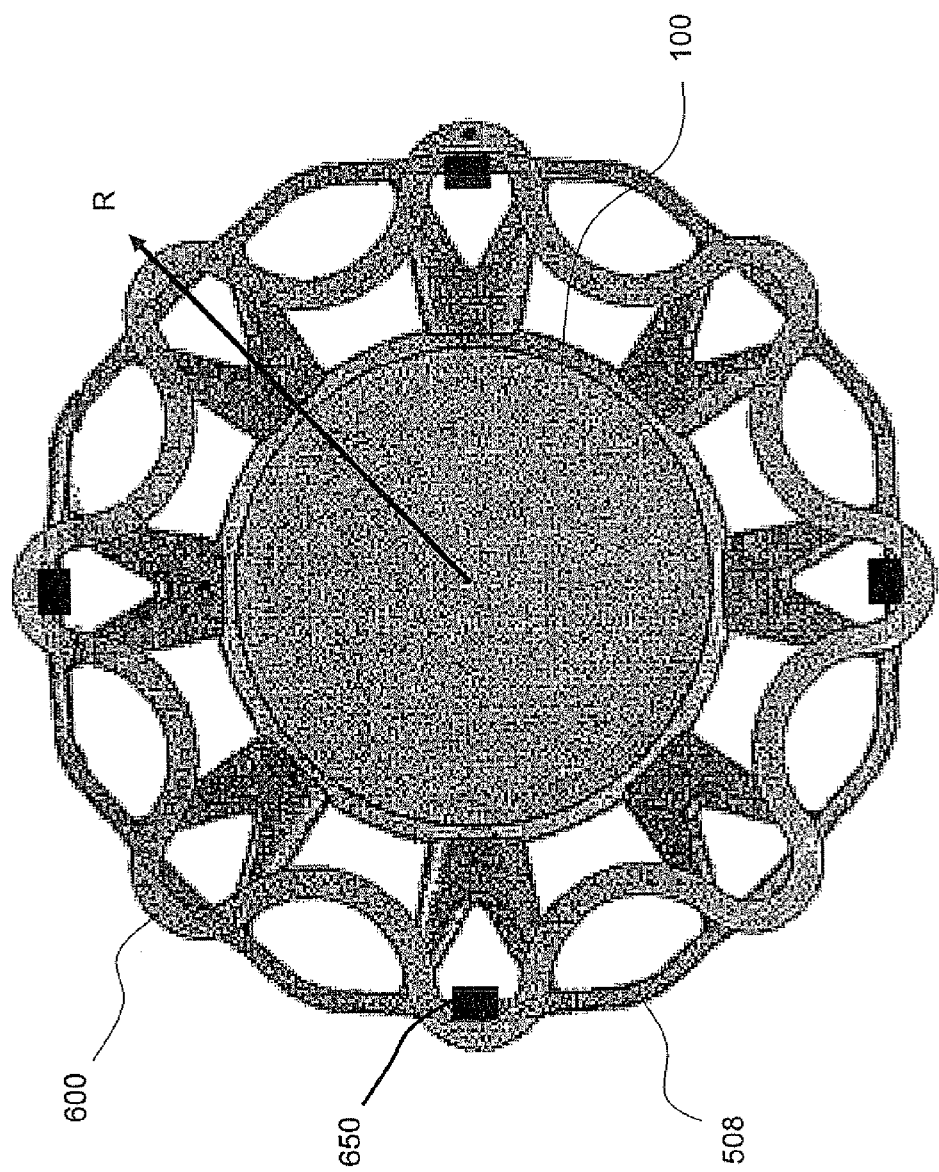
FIG. 10 illustrates a top-view of one embodiment of a device comprising a capsular ring coupled to a haptic.

FIG. 10 illustrates a top-view of one embodiment of a device 1000 comprising capsular ring 600 coupled to haptic 508 and optic 100.

Beneficially, device 1000 is sized to fit within a capsular bag of a human eye and functions as an accommodating intraocular lens (A-IOL). In particular, capsular ring 600 is adapted to transfer deforming forces imposed on the capsular bag by ciliary muscle force from zonules, to optic 100 via haptic 508. In one embodiment, in device 1000 capsular ring 600 includes tabs 650 that are adapted to clip into the generally triangular shaped openings 526 of haptic 508. Beneficially, capsular ring 600 is made of the same material as haptic 508 and/or optic 100. However, in some embodiments capsular ring 600 may be made of a different material than haptic 508 and/or optic 100.

In one exemplary embodiment, during an implantation procedure the lens material is broken up and vacuumed out of the eye and then capsular ring 600 is inserted into the capsular bag to keep it intact and to prevent it from collapsing. Then, a device comprising haptic 508 and optic 100 is implanted into the capsular bag and manipulated into a desired location and position so as to be in a supporting relationship with capsular ring 600, such as that illustrated in FIG. 10. Tabs 650 of capsular ring 600 may be snapped into the generally triangular shaped openings 326 of haptic 300 to assist in the positioning within the capsular bag.

A similar device to device 1000 shown in FIG. 10 can be produced using haptic 308 rather than haptic 508, and a description thereof will not be repeated here.

Figure 11:
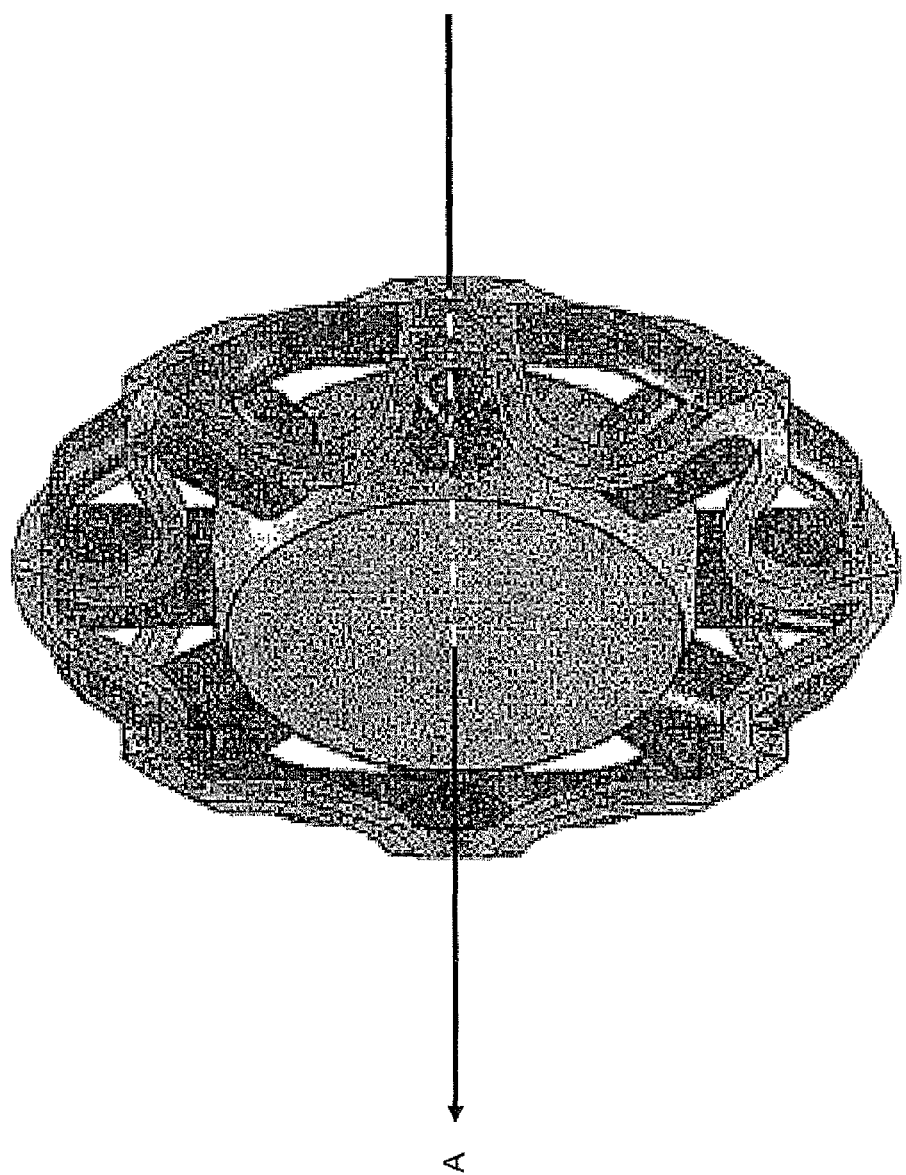
FIG. 11 illustrates an isometric view of the device of FIG. 10.
Figure 12:
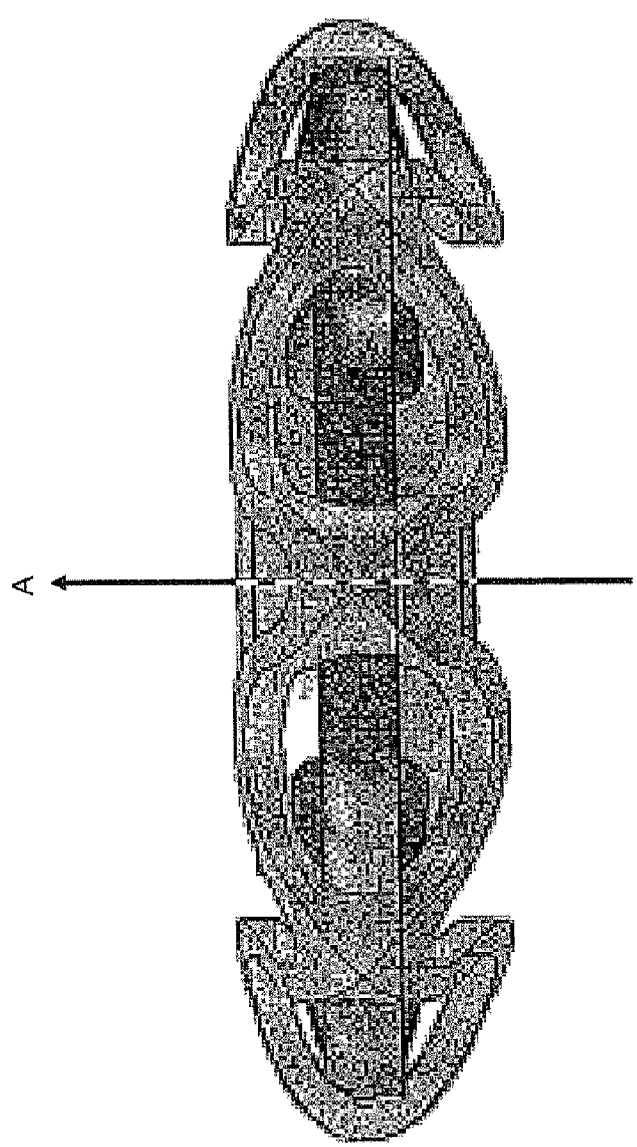
FIG. 12 illustrates a side-view of the device of FIG. 10.
Figure 13:
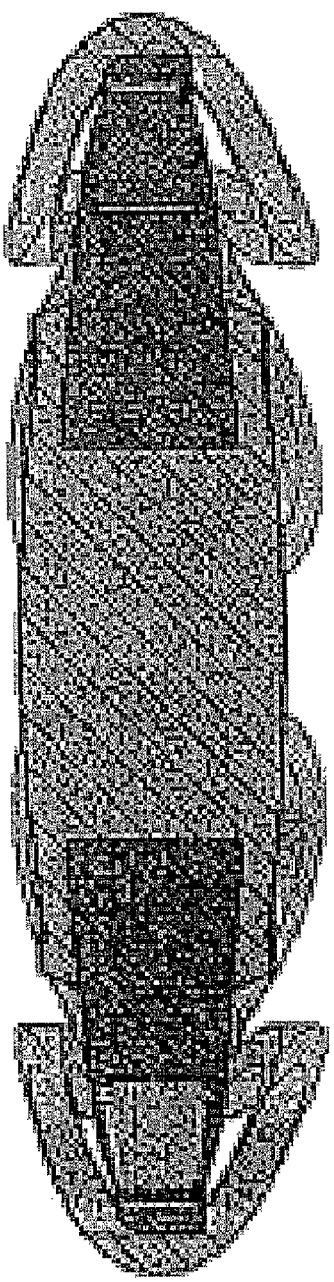
FIG. 13 illustrates a cross-sectional side-view of the device of FIG. 10.

FIG. 11 illustrates an isometric view of device 1000. FIG. 12 illustrates a side-view of device 1000. FIG. 13 illustrates a cross-sectional view of device 1000.

Figure 14:
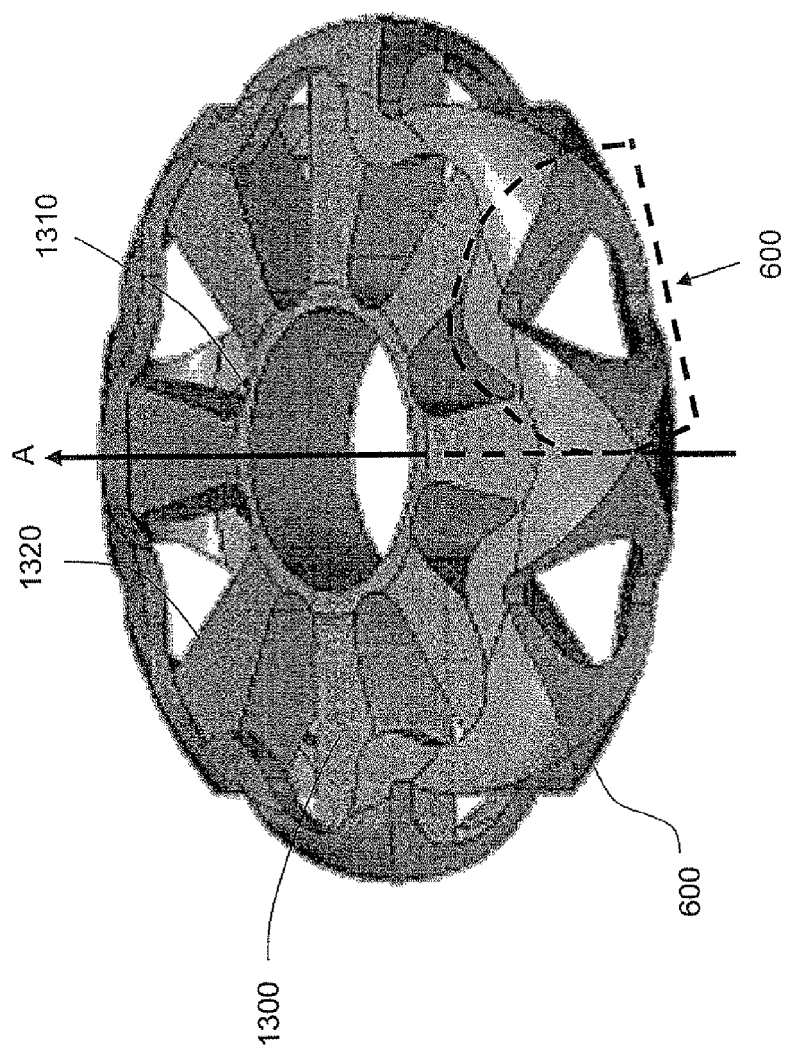
FIG. 14 illustrates an isometric view of another embodiment of a device comprising a capsular ring coupled to a haptic.

FIG. 14 illustrates an isometric view of another embodiment of a device 1400 comprising capsular ring 600 coupled to a haptic 1300.

Haptic 1300 includes a ring portion 1310 and a plurality of radial arms 1320. Ring portion 1310 is adapted to surround a circumference of an optic such as optic 100 (not shown in FIG. 14). Each radial arm 1320 has a first end connected to ring portion 1310 and a second end extending radially therefrom so as to come into contact with ringlets 605 of capsular ring 600.

Figure 15:
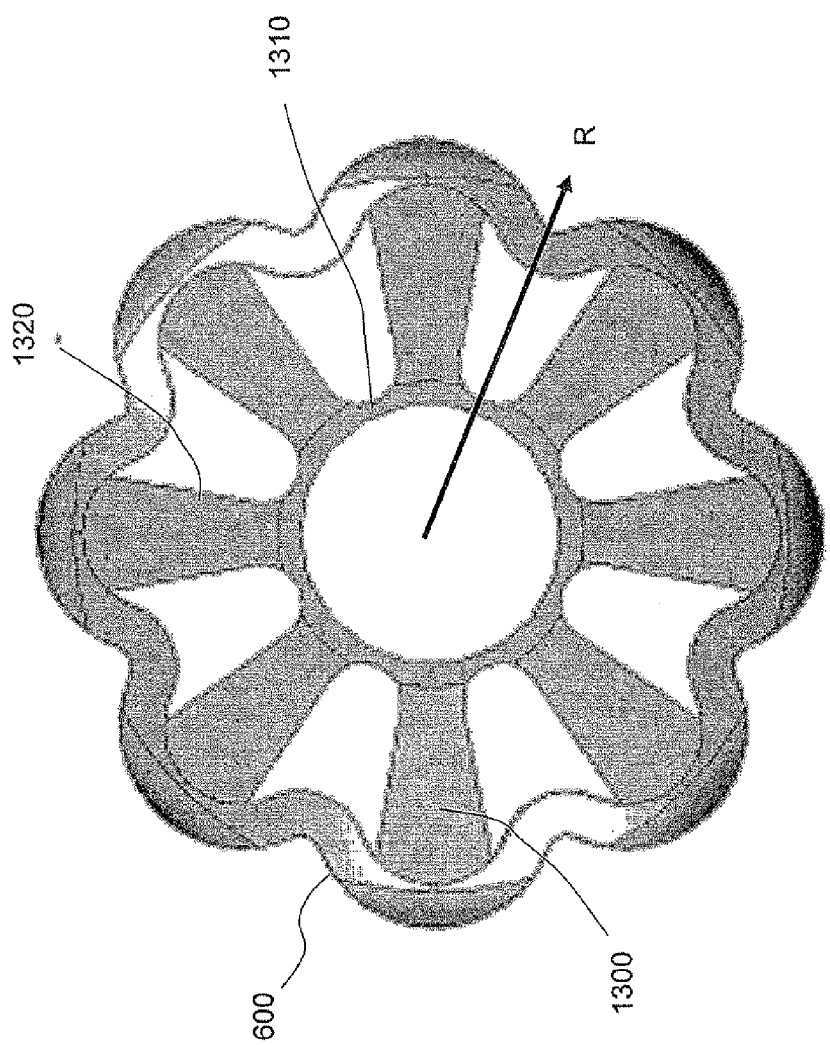
FIG. 15 illustrates a top-view of the device of FIG. 14.
Figure 16:
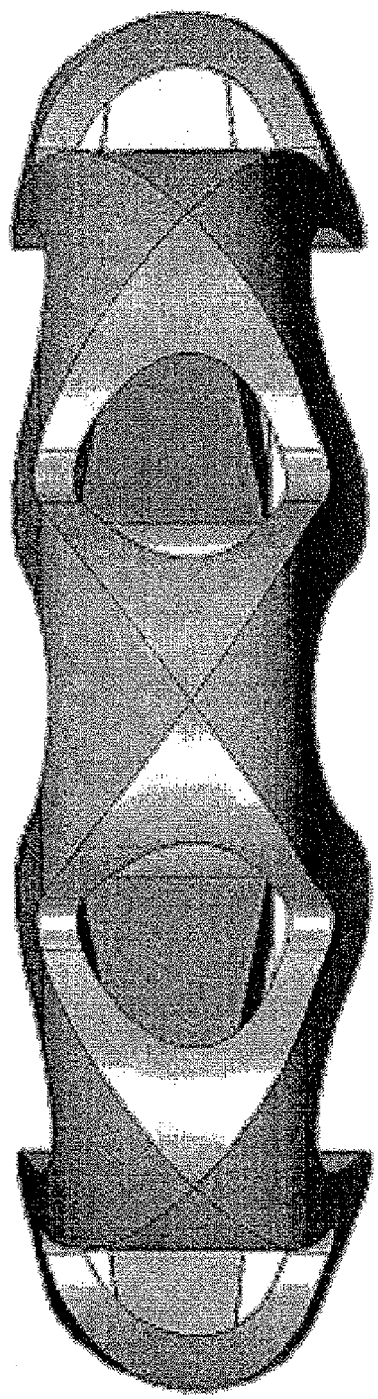
FIG. 16 illustrates a side-view of the device of FIG. 14.
Figure 17:
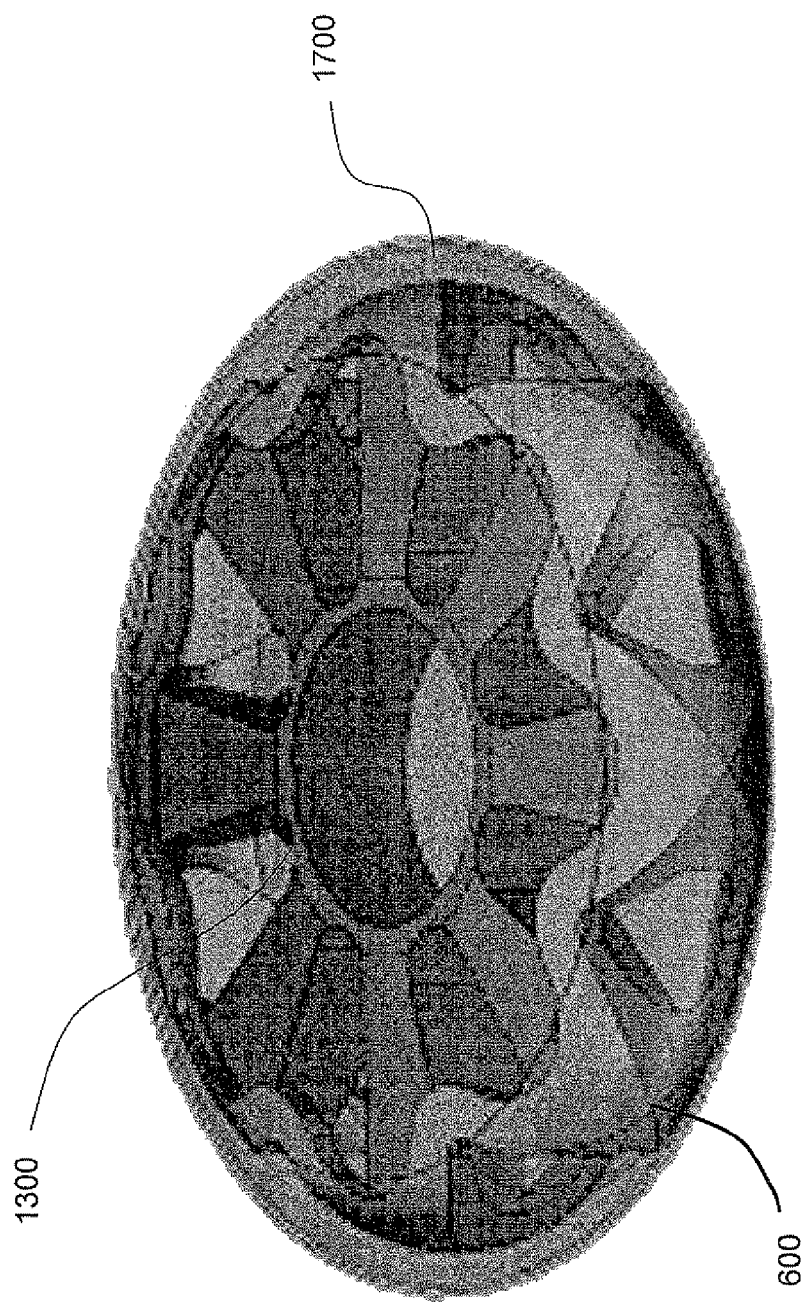
FIG. 17 illustrates an isometric view of the device of FIG. 14 in a capsular bag.
Figure 18:
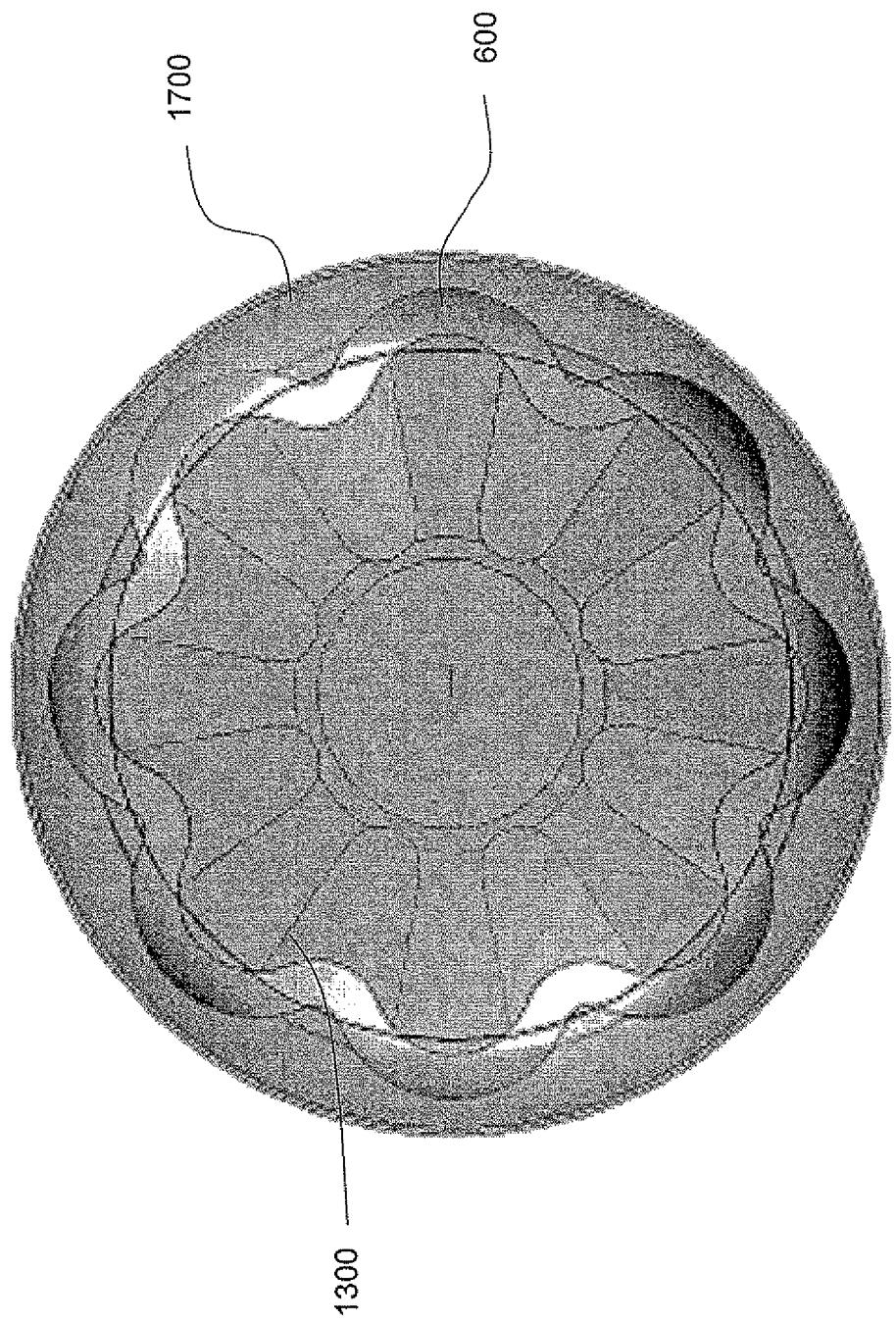
FIG. 18 illustrates a top-view of the device of FIG. 14 in a capsular bag.
Figure 19:
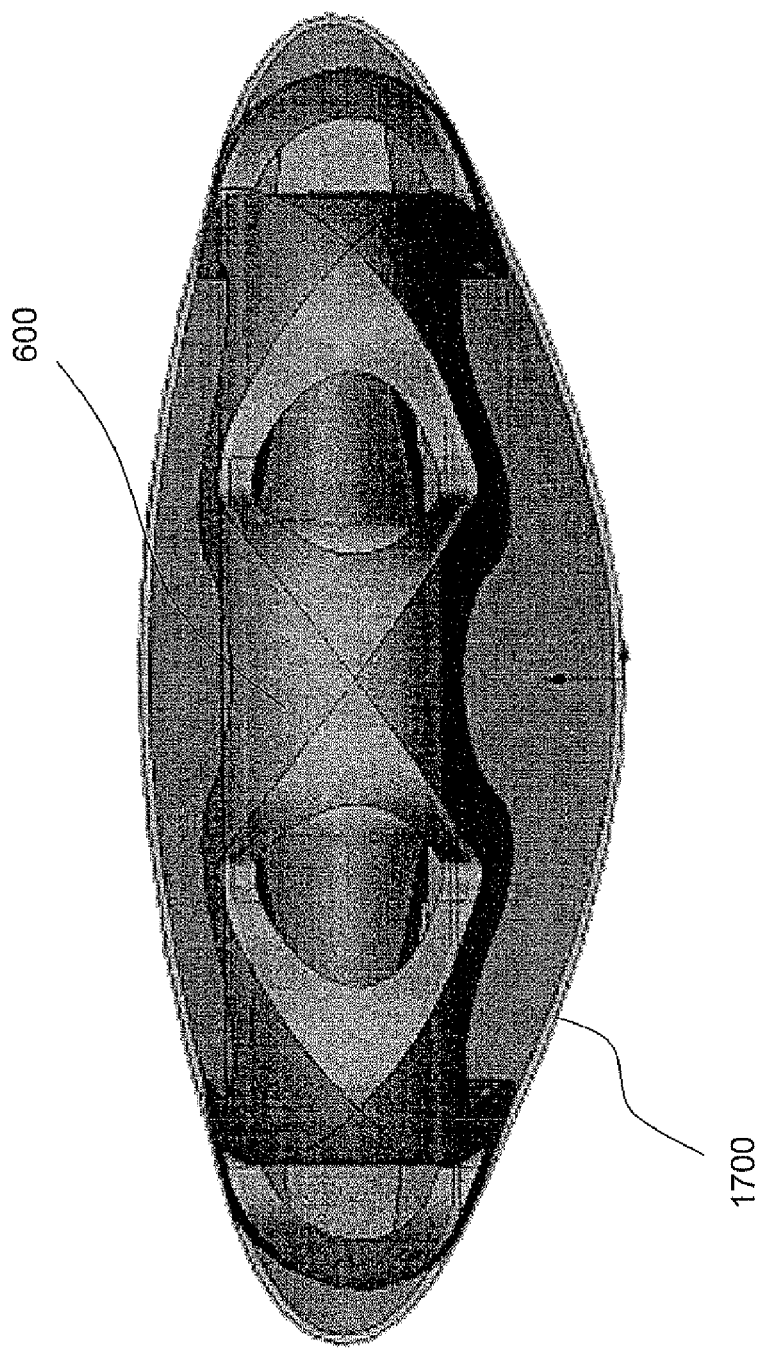
FIG. 19 illustrates a side-view of the device of FIG. 14 in a capsular bag.

FIG. 15 illustrates a top-view of device 1400. FIG. 16 illustrates a side-view of device 1400. FIG. 17 illustrates an isometric view of device 1400 in a capsular bag. FIG. 18 illustrates a top-view device 1400 in a capsule bag. FIG. 19 illustrates a side-view of device 1400 in a capsular bag.

Figure 20:
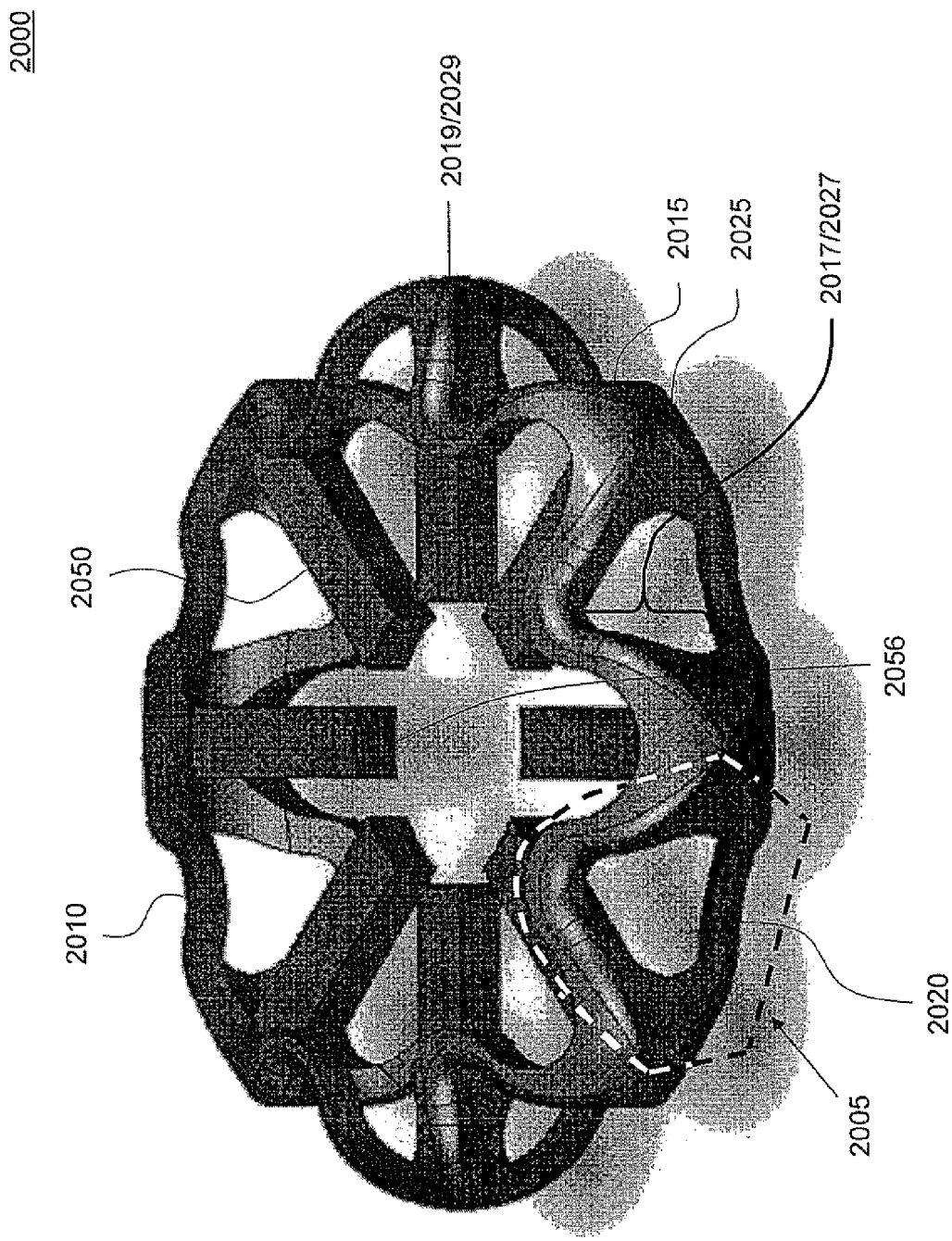
FIG. 20 illustrates an isometric view of another embodiment of a capsular ring.
Figure 21:
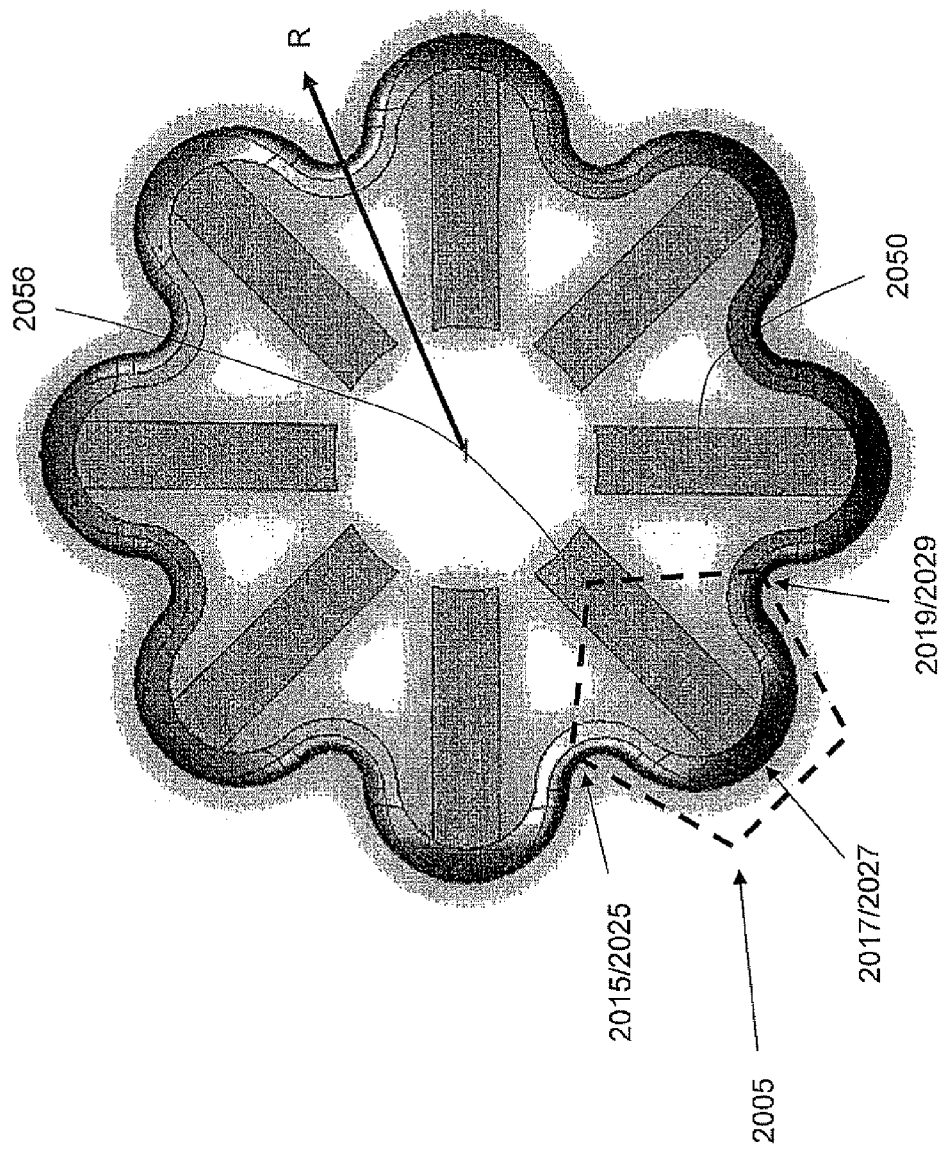
FIG. 21 illustrates a top-view of the capsular ring of FIG. 20.
Figure 22:
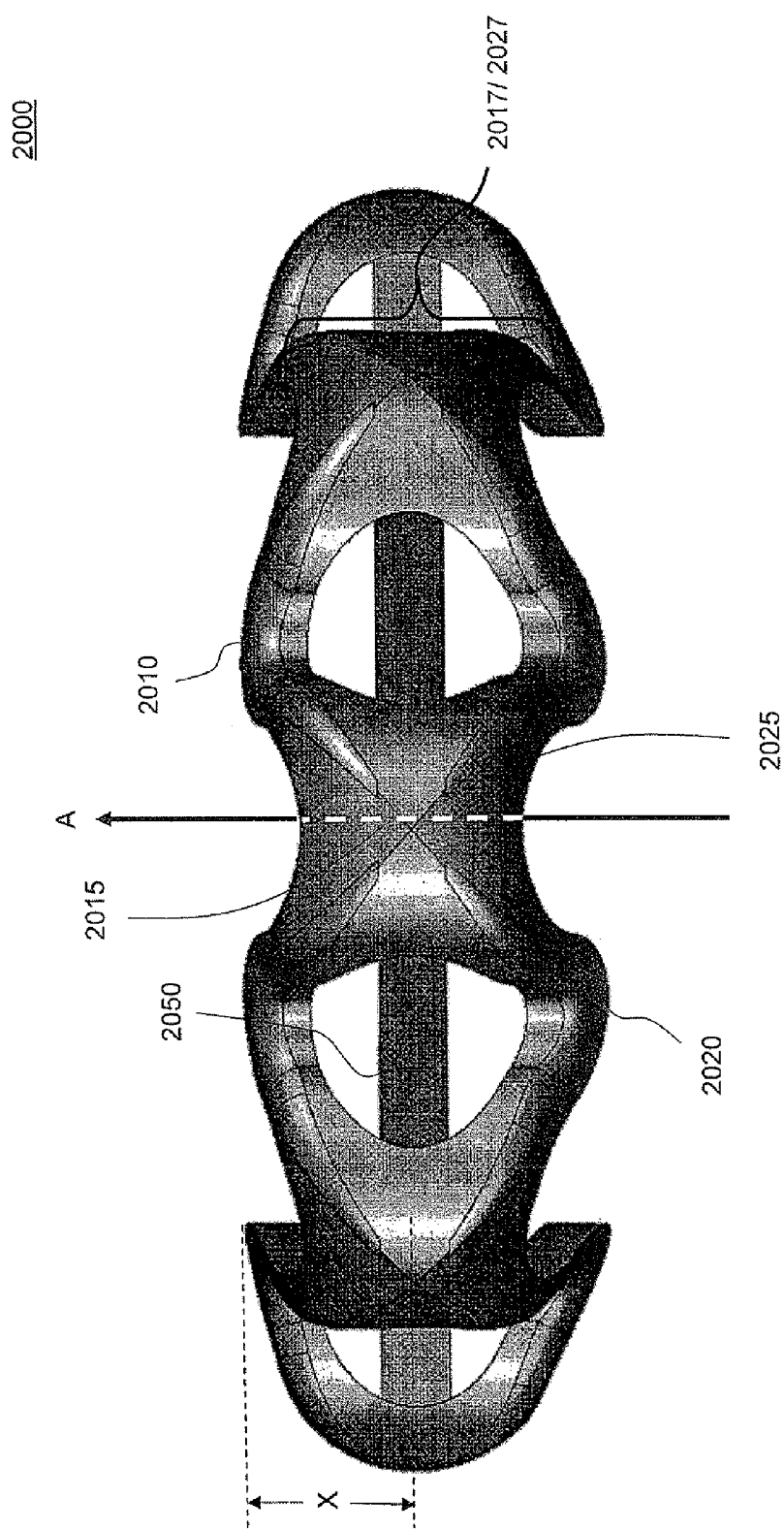
FIG. 22 illustrates a side-view of the capsular ring of FIG. 20.

FIG. 20 illustrates an isometric view of another embodiment of a capsular ring 2000. FIG. 21 illustrates a top-view of capsular ring 2000. FIG. 22 illustrates a side-view of capsular ring 2000.

Capsular ring 2000 includes a plurality of ringlets 2005 connected together in a closed ring shape about a longitudinal axis "A." Each ringlet 2005 includes a first element 2010 and a second element 2020.

The first and second elements 20610 and 2020 each extend from a respective first end 2015/2025 thereof through a central portion 2017/2027 thereof to a second end 2019/2029 thereof. The first ends 2015/2025 and second ends 2019/2029 of elements 2010 and 2020 of each ringlet 2005 are disposed at radially outer positions with respect to a radial direction "R" (see FIG. 21) of the capsular ring 2000 than the respective central portions 2017/2027 of elements 2010 and 2020. The central portion 2017/2027 of each respective element 2010/2020 is longitudinally displaced by an amount "X" (see FIG. 22) from the first end 2015/2025 and second end 2019/2029 thereof First and second elements 2010 and 2020 are joined together at the first ends 2015 and 2025 and at the second ends second ends 2019 and 2029, and are separated and spaced apart from each other at the central portions 2017 and 2027.

Capsular ring 2000 further includes a plurality of radial arms 2050. Radial arms 2050 each have a first end disposed at an area where adjacent ringlets 2005 are joined together, and a second end 2056 extending so as to contact a side of an optic such as optic 100 (not shown in FIGS. 20-22).

The addition of radial arms 2050 allow capsular ring 2000 to function as a haptic, thereby eliminating the need for a separate haptic, such as haptics 300, 500 or 1300 described above. In some embodiments, radial arms 2050 may be considered to comprise a plurality of camming projections extending from first and second ring portions 2010 and 2020, so as to cooperatively engage the optic. In one embodiment the radial dimension of a device can be adjusted by turning the optic against the camming projections 2050. In another embodiment, the optic has annular recesses around its side edge, and radial arms 2050 extend or protrude into these annular recesses, instead of merely contacting the optic at a cylindrical edge parallel to the optical axis "A."

Capsular ring 2000 is similar to capsular ring 600, with the exception of the radial arms 2050. Therefore, a detailed description of the various beneficial features, characteristics, and embodiments described above with respect to capsular ring 600 will not be repeated.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

I claim:

1. A device, comprising:
   a plurality of ringlets disposed about a longitudinal axis and connected together to form a ring, each ringlet comprising:
      a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element, and
      a second element extending from a first end thereof through a central portion thereof to a second end thereof, where the first arid second ends of the second element are disposed at radially outer positions with respect to the ring than the central portion of the second element, and where the central portion of the second element is longitudinally displaced from the first and second ends of the second element,
   wherein the first and second elements are separated and spaced apart from each other at the central portions thereof and are joined together at the first ends thereof and the second ends thereof,
   wherein the plurality of ringlets are connected together such that the first ends of the elements of one ringlet are connected to the second ends of the elements of an adjacent ringlet;
   an optic; and
   a haptic comprising a plurality of radial arms, each radial arm having a first end in contact with a side of the optic, the radial arm extending radially therefrom, and a ring portion surrounding a circumference of the optic and connected to second ends of each of the radial arms,
   wherein a radially peripheral portion of the haptic is adapted to be held by the ringlets, and
   wherein the haptic is configured to transmit forces to alter at least one of a shape and a thickness of the optic,
   wherein the device is configured to respond to force applied by a capsular bag to facilitate accommodation of the optic.

2. The device of claim 1, wherein the device is more rigid in a direction along the longitudinal axis of the device than in a radial direction.

3. The device of claim 1, wherein the device is sized to fit within the capsular bag of a human eye and to hold the capsular bag open, and wherein when the device is inserted into the capsular bag, the device is adapted to respond to force applied by the capsular bag to change a thickness of the device in a direction along the longitudinal axis of the device.

4. The device of claim 1, wherein the first and second elements of at least two of the ringlets include tabs adapted for holding the ring portion of the haptic.

5. The device of claim 1, wherein the haptic is stiffer than the optic.

6. A device comprising:
   a plurality of ringlets disposed about a longitudinal axis and connected together to form a ring, each ringlet comprising:
      a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element; and
      a second element extending from a first end thereof through a central portion thereof to a second end thereof, where the first and second ends of the second element are disposed at radially outer positions with respect to the ring than the central portion of the second element, and where the central portion of the second element is longitudinally displaced from the first and second ends of the second element;
   wherein the first and second elements are separated and spaced apart from each other at the central portions thereof and are joined together at the first ends thereof and the second ends thereof;
   wherein the plurality of ringlets are connected together such that the first ends of the elements of one ringlet are connected to the second ends of the elements of an adjacent ringlet;
   an optic; and
   a haptic comprising:
      a radially peripheral portion adapted to be held by the ringlets;
      a ring portion surrounding a circumference of the optic; and
      a plurality of radial arms, each radial arm having a first end connected to the ring portion and a second end extending radially therefrom so as to come into contact with at least one of the ringlets;
   wherein the haptic is configured to transmit forces to alter at least one of a shape and a thickness of the optic, and
   wherein the device is configured to respond to force applied by a capsular bag to facilitate accommodation of the optic.

7. The device of claim 6, wherein the device is more rigid in a direction along the longitudinal axis of the device than in a radial direction.

8. The device of claim 6, wherein the device is sized to fit within the capsular bag of a human eye and to hold the capsular bag open, and wherein when the device is inserted into the capsular bag, the device is adapted to respond to force applied by the capsular bag to change a thickness of the device in a direction along the longitudinal axis of the device.

9. The device of claim 6, wherein the haptic is stiffer than the optic.

10. A device comprising:
    a plurality of ringlets disposed about a longitudinal axis and connected together to form a ring, each ringlet comprising:
       a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element; and
       a second element extending from a first end thereof through a central portion thereof to a second end thereof, where the first and second ends of the second element are disposed at radially outer positions with respect to the ring than the central portion of the second element, and where the central portion of the second element is longitudinally displaced from the first and second ends of the second element;

wherein the first and second elements are separated and spaced apart from each other at the central portions thereof and are joined together at the first ends thereof and the second ends thereof;

wherein the plurality of ringlets are connected together such that the first ends of the elements of one ringlet are connected to the second ends of the elements of an adjacent ringlet;

an optic; and a plurality of radial arms each having, an outer end disposed at an area where the first ends of the elements of one ringlet are connected to the second ends of the elements of an adjacent ringlet, and an inner end extending so as to be in contact with a side of the optic;

wherein the device is configured to respond to force applied by a capsular bag to facilitate accommodation of the device.

11. The device of claim 10, wherein the device is more rigid in a direction along the longitudinal axis of the device than in a radial direction.

12. The device of claim 10, wherein the device is sized to fit within the capsular bag of a human eye and to hold the capsular bag open, and wherein when the device is inserted into the capsular bag, the device is adapted to respond to force applied by the capsular bag to change a thickness of the device in a direction along the longitudinal axis of the device.

13. A device comprising:

a plurality of ringlets disposed about a longitudinal axis and connected together to form a ring, each ringlet comprising:

a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element; and a second element extending from a first end thereof through a central portion thereof to a second end thereof, where the first and second ends of the second element are disposed at radially outer positions with respect to the ring than the central portion of the second element, and where the central portion of the second element is longitudinally displaced from the first and second ends of the second element;

wherein the first and second elements are separated and spaced apart from each other at the central portions thereof and are joined together at the first ends thereof and the second ends thereof;

wherein the plurality of ringlets are connected together such that the first ends of the elements of one ringlet are connected to the second ends of the elements of an adjacent ringlet;

an optic; and a plurality of camming projections extending from the ringlets so as to cooperatively engage the optic, wherein a radial dimension of the device can be adjusted by turning the optic against the camming projections; and wherein the device is configured to respond to force applied by the capsular bag to facilitate accommodation of the device.

14. The device of claim 13, wherein the device is more rigid in a direction along the longitudinal axis of the device than in a radial direction.

15. The device of claim 13, wherein the device is sized to fit within the capsular bag of a human eye and to hold the capsular bag open, and wherein when the device is inserted into the capsular bag, the device is adapted to respond to force applied by the capsular bag to change a thickness of the device in a direction along the longitudinal axis of the device.

16. A device for implantation into a capsular bag of an eye, the device comprising:

a ring element adapted to be inserted through an incision in the capsular bag and to hold open the capsular bag; and an optic adapted to be inserted into the capsular bag having the ring element inserted therein, and to be operatively engaged with the ring element so as to be held within the capsular bag, wherein the ring element has a longitudinal axis and comprises a plurality of ringlets connected together, each ringlet comprising:

a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element, and a second element extending from a first end thereof through a central portion thereof to a second end thereof, where the first and second ends of the second element are disposed at radially outer positions with respect to the ring than the central portion of the second element, and where the central portion of the second element is longitudinally displaced from the first and second ends of the second element, wherein the first and second elements are separated and spaced apart from each other at the central portions thereof and are joined together at the first ends thereof and the second ends thereof, wherein the plurality of ringlets are connected together such that each of the first ends of the elements of one ringlet are connected to a corresponding second end of the elements of an adjacent ringlet, wherein the ring element includes a plurality of radial arms each extending inwardly so as to engage the optic.

17. The device of claim 16, wherein the ring element is more rigid in a direction along the longitudinal axis of the ring element than in a radial direction.

18. The device of claim 16, wherein the ring element is adapted to respond to force applied by the capsular bag to change a thickness of the ring element in a direction along the longitudinal axis of the ring element.

19. A device for implantation into a capsular bag of an eye, the device comprising:

a ring element adapted to be inserted through an incision in the capsular bag and to hold open the capsular bag;

an optic adapted to be inserted into the capsular bag having the ring element inserted therein, and to be operatively engaged with the ring element so as to be held within the capsular bag, wherein the ring element has a longitudinal axis and comprises a plurality of ringlets connected together, each ringlet comprising:

a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element, and a second element extending from a first end thereof through a central portion thereof to a second end thereof, where the first and second ends of the second element are disposed at radially outer positions with respect to the ring than the central portion of the second element, and where the central portion of the second element is longitudinally displaced from the first and second ends of the second element, wherein the first and second elements are separated and spaced apart from each other at the central portions thereof and are joined together at the first ends thereof and the second ends thereof, wherein the plurality of ringlets are connected together such that each of the first ends of the elements of one ringlet are connected to a corresponding second end of the elements of an adjacent ringlet, and a plurality of camming projections extending from the ring element so as to cooperatively engage the optic, wherein a radial dimension of the ring element can be adjusted by turning the optic against the camming projections.

20. The device of claim 19, wherein the ring element is more rigid in a direction along the longitudinal axis of the ring element than in a radial direction.

21. The device of claim 19, wherein the ring element is adapted to respond to force applied by the capsular bag to change a thickness of the ring element in a direction along the longitudinal axis of the ring element.

22. A device for implantation into a capsular bag of an eye, the device comprising:

a ring element adapted to be inserted through an incision in the capsular bag and to hold open the capsular bag;

an optic adapted to be inserted into the capsular bag having the ring element inserted therein, and to be operatively engaged with the ring element so as to be held within the capsular bag, wherein the ring element has a longitudinal axis and comprises a plurality of ringlets connected together, each ringlet comprising:

a first element extending from a first end thereof through a central portion thereof to a second end thereof, where the first and second ends of the first element are disposed at radially outer positions with respect to the ring than the central portion of the first element, and where the central portion of the first element is longitudinally displaced from the first and second ends of the first element, and a second element extending from a first end thereof through a central portion thereof to a second end thereof, where the first and second ends of the second element are disposed at radially outer positions with respect to the ring than the central portion of the second element, and where the central portion of the second element is longitudinally displaced from the first and second ends of the second element, wherein the first and second elements are separated and spaced apart from each other at the central portions thereof and are joined together at the first ends thereof and the second ends thereof, wherein the plurality of ringlets are connected together such that each of the first ends of the elements of one ringlet are connected to a corresponding second end of the elements of an adjacent ringlet, and a haptic including a portion protruding into the optic, wherein a radially peripheral portion of the haptic is adapted to be held by the ring element, wherein the ring element includes tabs adapted for holding the haptic.

23. The device of claim 22, wherein the haptic is configured to transmit forces to alter at least one of a shape and a thickness of the optic.

24. The device of claim 22, wherein the ring element is more rigid in a direction along the longitudinal axis of the ring element than in a radial direction.

25. The device of claim 22, wherein the ring element is adapted to respond to force applied by the capsular bag to change a thickness of the ring element in a direction along the longitudinal axis of the ring element.

* * * * *